US012718945B2

(12) United States Patent
Nassiri et al.

(10) Patent No.: US 12,718,945 B2
(45) Date of Patent: Aug. 25, 2026

(54) RADIOMIC-BASED MACHINE LEARNING ALGORITHM TO RELIABLY DIFFERENTIATE BENIGN RENAL MASSES FROM RENAL CELL CARCINOMA

(71) Applicant: UNIVERSITY OF SOUTHERN CALIFORNIA, Los Angeles, CA (US)

(72) Inventors: Nima Nassiri, Los Angeles, CA (US); Giovanni Cacciamani, Los Angeles, CA (US); Steven Cen, Los Angeles, CA (US); Vinay Duddalwar, Los Angeles, CA (US); Inderbir Gill, Los Angeles, CA (US); Darryl Hwang, Los Angeles, CA (US); Marissa Maas, Los Angeles, CA (US); Bino Varghese, Los Angeles, CA (US); Felix Yuh-Chern Yap, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 199 days.

(21) Appl. No.: 18/286,918

(22) PCT Filed: May 27, 2022

(86) PCT No.: PCT/US2022/031342

§ 371 (c)(1),
(2) Date: Oct. 13, 2023

(87) PCT Pub. No.: WO2022/251633

PCT Pub. Date: Dec. 1, 2022

(65) Prior Publication Data

US 2024/0194339 A1 Jun. 13, 2024

Related U.S. Application Data

(60) Provisional application No. 63/194,846, filed on May 28, 2021.

(51) Int. Cl.
*G16H 50/20* (2018.01)
*G06T 7/00* (2017.01)
(Continued)

(52) U.S. Cl.
CPC ........... *G16H 50/20* (2018.01); *G06T 7/0012* (2013.01); *G06T 7/40* (2013.01); *G06T 7/62* (2017.01);
(Continued)

(58) Field of Classification Search
CPC . G06T 2207/30096; G06T 2207/10072; G06T 2207/20084; G06T 7/0012;
(Continued)

(56) References Cited

U.S. PATENT DOCUMENTS 9,092,691 B1 * 7/2015 Beaumont .............. G06V 10/25
2017/0351939 A1 * 12/2017 Madabhushi ............. G06T 7/11
(Continued)

FOREIGN PATENT DOCUMENTS

CN 109035197 12/2018
CN 110957034 4/2020
KR 101824691 B1 * 2/2018 ............... A61B 6/03

OTHER PUBLICATIONS

KR-101824691-B1: English Translation (Year: 2018).*
(Continued)

*Primary Examiner* — Sumati Lefkowitz
*Assistant Examiner* — Aaron Joseph Sorrin
(74) *Attorney, Agent, or Firm* — Meunier Carlin & Curfman LLC

(57) ABSTRACT

A system, computer readable medium, apparatus and/or method for non-invasive, non-surgical, digital biopsy. The system, computer readable medium, apparatus and/or method accurately predicts benign kidney lesions from cancers in a patient. A processor may receive patient clinical
(Continued)

factors, texture analysis of computer-tomographic imaging, and an artificial intelligence learning model. By implementing artificial intelligence, the processor may then predict or determine a probability of kidney cancer in the patient using the patient clinical factors, the texture analysis of computer-tomographic imaging, and the artificial intelligence learning model. Notably, the prediction is performed without needing invasive biopsy surgery and subsequent pathology analysis to arrive at a diagnosis but relies on radiomics metrics.

15 Claims, 14 Drawing Sheets

(51) Int. Cl.
*G06T 7/40* (2017.01)
*G06T 7/62* (2017.01)
*G16H 30/40* (2018.01)

(52) U.S. Cl.
CPC ... *G16H 30/40* (2018.01); *G06T 2207/10081* (2013.01); *G06T 2207/10104* (2013.01); *G06T 2207/10108* (2013.01); *G06T 2207/20081* (2013.01); *G06T 2207/30084* (2013.01); *G06T 2207/30096* (2013.01)

(58) Field of Classification Search
CPC ... G06T 7/40; G06T 7/62; G06T 2207/10081; G06T 2207/10104; G06T 2207/10108; G06T 2207/20081; G06T 2207/30084; G16H 50/20; G16H 50/30; G16H 10/60; G16H 70/60; G16H 30/40; G06V 10/82; G06V 10/764; G06V 2201/03; G06V 10/80; A61B 6/5217; A61B 2576/02; A61B 5/004; A61B 5/201; G01N 2800/7028; G06N 20/20
See application file for complete search history.

(56) References Cited

U.S. PATENT DOCUMENTS

| | | | | |
|---|---|---|---|---|
| 2018/0068083 | A1* | 3/2018 | Cohen | G16H 50/20 |
| 2018/0253841 | A1* | 9/2018 | Madabhushi | G06T 7/162 |
| 2020/0005901 | A1 | 1/2020 | Cohen et al. | |

OTHER PUBLICATIONS

Erdim C, Yardimci AH, Bektas CT, Kocak B, Koca SB, Demir H, Kilickesmez O. Prediction of Benign and Malignant Solid Renal Masses: Machine Learning-Based CT Texture Analysis. Acad Radiol. Oct. 2020;27(10):1422-1429. doi: 10.1016/j.acra.2019.12.015. Epub Feb. 1, 2020. PMID: 32014404. (Year: 2020).*

Kolthammer JA, Su KH, Grover A, Narayanan M, Jordan DW, Muzic RF. Performance evaluation of the Ingenuity TF PET/CT scanner with a focus on high count-rate conditions. Phys Med Biol. Jul. 21, 2014;59(14):3843-59. doi: 10.1088/0031-9155/59/14/3843. Epub Jun. 23, 2014. PMID: 24955921; PMCID: PMC4457340. (Year: 2014).*

International Search Report and Written Opinion for International PCT Patent Application No. PCT/US2022/031342, Sep. 27, 2022, 9 pages.

Erdim et al., Prediction of benign and malignant solid renal masses: machine learning-based CT texture analysis. Academic radiology, 2020, vol. 27, No. 10, pp. 1422-1429.

* cited by examiner

Variables of Importance - Robust Model

TNM Stage
Grade

Intensity 6.52% 14.29%
GLSZM 3D 4.35% 4.76%
GLSZM 2D 4.35% 7.14%
GLRLM 3D 4.35% 2.38%
GLRLM 2D 6.52% 14.29%
GLDM 3D 8.70% 2.38%
GLDM 2D 34.78% 9.52%
GLCM 3D 8.70% 14.29%
GLCM 2D 21.74% 30.95%

0.00% 5.00% 10.00% 15.00% 20.00% 25.00% 30.00% 35.00% 40.00%

RADIOMIC-BASED MACHINE LEARNING ALGORITHM TO RELIABLY DIFFERENTIATE BENIGN RENAL MASSES FROM RENAL CELL CARCINOMA

CROSS-REFERENCE TO RELATED APPLICATIONS

This application is based upon and claims priority to U.S. provisional patent application 63/194,846 entitled "A RADIOMIC-BASED MACHINE LEARNING ALGORITHM TO RELIABLY DIFFERENTIATE BENIGN RENAL MASSES FROM RENAL CELL CARCINOMA" and filed on May 28, 2021, the entire content of which is incorporated herein by reference.

BACKGROUND

1. Field

This disclosure relates generally to medical imaging technology, and more specifically, to machine learning to differentiate and classify benign and cancerous masses in medical images.

2. Description of the Related Art

Surgery remains the current gold standard for both the definitive diagnosis and treatment of kidney tumors. This approach subjects approximately a quarter of patients, who will ultimately have benign pathology, to surgery. While large renal masses may need resection for symptoms, overtreatment is not uncommon, and the incidence of benign pathology after surgery for SRMs (tumors<4 cm) remains as high as 30%. Though percutaneous biopsy may provide an accurate pre-operative diagnosis, not all tumors can be safely biopsied, either because of patient or tumor-specific factors, and utility remains limited by non-diagnostic potential. Similarly, adjunctive molecular imaging modalities remain investigational and costly. Thus, there is a need for accurate pre-surgical risk stratification, such as provided by the systems and methods herein.

SUMMARY

A non-invasive, non-surgical, digital biopsy method for accurately predicting benign kidney lesions from cancers in a patient is provided. The method may include receiving, at a processor, patient clinical factors, texture analysis of computer-tomographic imaging, and an artificial intelligence learning model. The method may include predicting or determining, using the processor, a probability of kidney cancer in the patient using the patient clinical factors, the texture analysis of computer-tomographic imaging, and the artificial intelligence learning model.

The method may include various other aspects as well. For instance, in various embodiments, using the patient clinical factors, the texture analysis of computer-tomographic imaging, and the artificial intelligence learning model yields a highly predictive model that can accurately differentiate kidney cancer from benign kidney masses. In various embodiments, the patient clinical factors include at least one of age, gender, race, co-morbid conditions, local symptoms at diagnosis, smoking status, family history, renal function, renal mass size or tumor-specific variables. Moreover, the texture analysis of computer-tomographic imaging may include performing two-dimensional shape and texture analysis on a largest tumor diameter within each imaging plane or performing three-dimensional shape and texture analysis on an entire tumor volume. The texture analysis of computer-tomographic imaging may include molecular imaging using radionuclide tagged probes detected with positron emitted tomography or single photon emission computed tomography.

The artificial intelligence learning model may include image analysis to increase the accuracy of the probability of kidney cancer in the patient. The artificial intelligence learning model may include radiomic-based predictive modeling. The artificial intelligence learning model may include a machine-learning predictive model that incorporates radiomic analysis.

A non-transitory computer-readable medium comprising computer readable instructions, is provided. The instructions, when executed by a processor, cause the processor to perform operations for conducting a non-invasive, non-surgical, digital biopsy method for accurately predicting benign kidney lesions from cancers in a patient. The operations may include receiving, at the processor, patient clinical factors, texture analysis of computer-tomographic imaging, and an artificial intelligence learning model. The operations may include predicting or determining, using the processor, a probability of kidney cancer in the patient using the patient clinical factors, the texture analysis of computer-tomographic imaging, and the artificial intelligence learning model.

In various instances, the operations further include wherein using the patient clinical factors, the texture analysis of computer-tomographic imaging, and the artificial intelligence learning model yields a highly predictive model that can accurately differentiate kidney cancer from benign kidney masses. The operations may include wherein the patient clinical factors include at least one of age, gender, race, co-morbid conditions, local symptoms at diagnosis, smoking status, family history, renal function, renal mass size or tumor-specific variables.

In further instances, the operations include wherein the texture analysis of computer-tomographic imaging includes performing two-dimensional shape and texture analysis on a largest tumor diameter within each imaging plane or performing three-dimensional shape and texture analysis on an entire tumor volume. The texture analysis of computer-tomographic imaging may include molecular imaging using radionuclide tagged probes detected with positron emitted tomography or single photon emission computed tomography.

In various embodiments, the operations include wherein the artificial intelligence learning model includes image analysis to increase the accuracy of the probability of kidney cancer in the patient. The artificial intelligence learning model may include radiomic-based predictive modeling. The artificial intelligence learning model may include a machine-learning predictive model that incorporates radiomic analysis.

A system for non-invasive, non-surgical, digital biopsy for accurately predicting benign kidney lesions from cancers in a patient is provided. The system may include a diagnostic scan source having a computer-tomographic image scanner configured to generate a plurality of computer-tomographic images corresponding to at least one kidney of a patient. The system may include a server having a memory storing a plurality of patient clinical factors. The system may include a processor connected to the diagnostic scan source and the server and configured to receive at the processor the patient clinical factors and the plurality of computer-tomographic images. The processor is configured to predicting or determining a probability of kidney cancer in the at least one kidney of the patient using the patient clinical factors, a texture analysis of the plurality of computer-tomographic images, and an artificial intelligence learning model.

In various embodiments of the system, using the patient clinical factors, the texture analysis of computer-tomographic imaging, and the artificial intelligence learning model yields a highly predictive model that can accurately differentiate kidney cancer from benign kidney masses. The patient clinical factors may include at least one of age, gender, race, co-morbid conditions, local symptoms at diagnosis, smoking status, family history, renal function, renal mass size or tumor-specific variables. The texture analysis of computer-tomographic imaging may include performing two-dimensional shape and texture analysis on a largest tumor diameter within each imaging plane or performing three-dimensional shape and texture analysis on an entire tumor volume.

BRIEF DESCRIPTION OF THE DRAWINGS

Other systems, methods, features, and advantages of the present invention will be or will become apparent to one of ordinary skill in the art upon examination of the following figures and detailed description.

DETAILED DESCRIPTION

A substantial proportion of patients undergo treatment for renal masses in scenarios where active surveillance or observation may be more appropriate. Radiomics-based machine learning platforms provide novel and non-obvious mechanisms to distinguish benign from malignant renal masses.

The disclosure herein will include a discussion of methods, results, and conclusions associated with various experiments, as well as disclosure of systems and methods for radiomics-based machine learning platforms.

Figure 1:
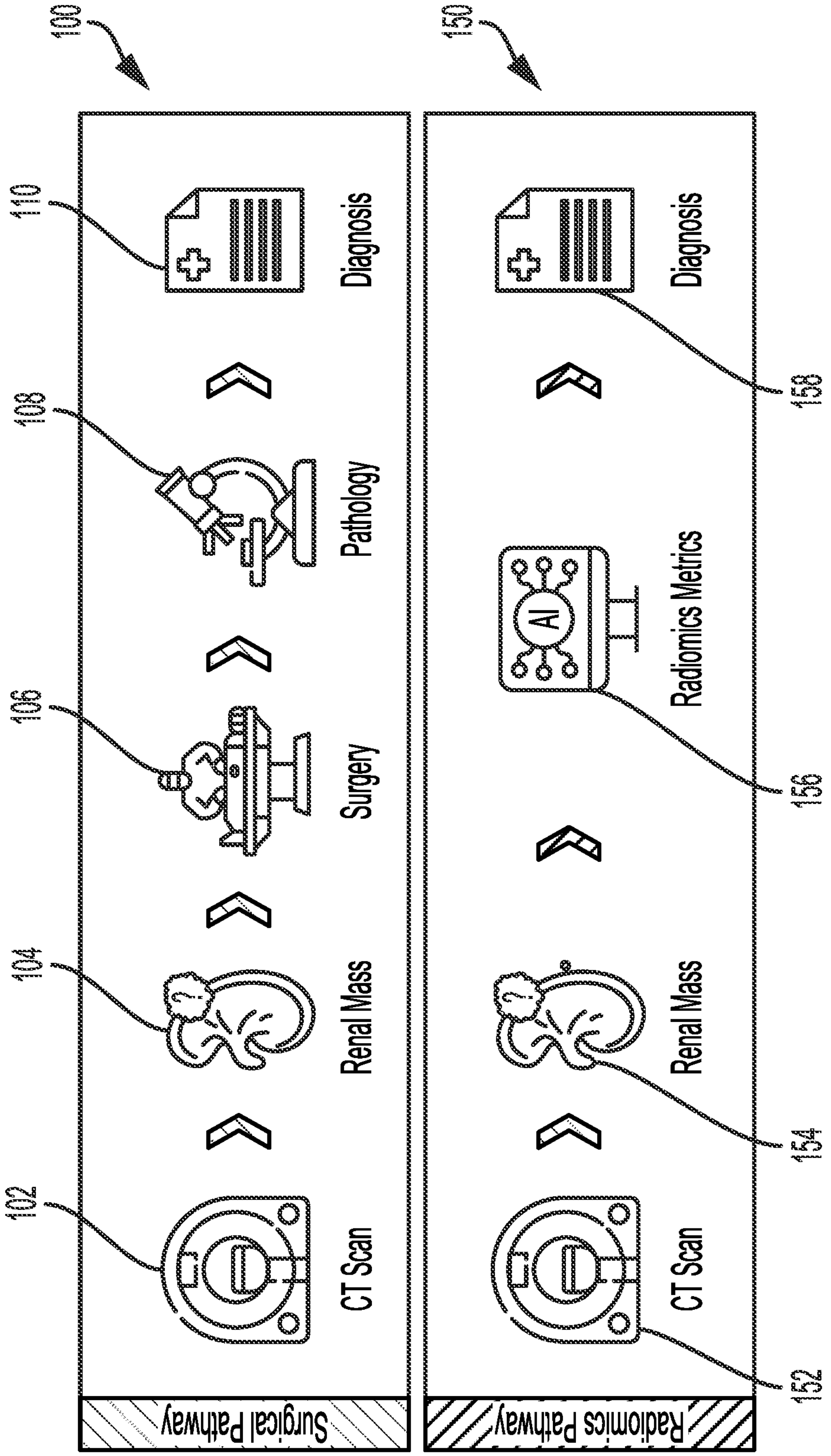
FIG. 1 illustrates conventional and radiomic diagnostic pathways, in accordance with various embodiments.

With reference to FIG. 1, a conventional surgical pathway 100 is illustrated for renal mass treatment. The conventional pathway may include a CT scan 102, which may detect a renal mass of unknown malignancy 104. Surgery is performed 106 to remove the renal mass and a pathology 108 analysis is performed to determine malignancy or non-malignancy. A diagnosis 110 is provided. However, to obtain diagnosis 110, a surgery 106 was carried out, along with corresponding risks, discomfort and costs. A radiomics pathway 150 is also shown. In various instances, a CT scan 152 is performed, which may detect a renal mass of unknown malignancy 154. Rather than surgery 106, instead, radiomics metrics are analyzed 156 via artificial intelligence technology according to systems and methods provided herein. A diagnosis is provided 158 without surgery 106.

Throughout the following discussion, various acronyms will be used. For convenience, an initial table. Table 0, is provided below reciting acronyms encountered herein:

TABLE 0

| Acronym | Meaning |
|---|---|
| Adaboost | Real Adaptive Boosting |
| AUC | Area Under the Curve |
| ccRCC | Clear Cell Renal Cell Carcinoma |
| CECT | Contrast-Enhanced Computed Tomography |
| CHA | Convex Hull Area Ratio |
| CHP | Convex Hull Perimeter Ratio |
| DCT | Discrete Cosine Transform |
| DICOM | Digital Imaging and communications in medicine |
| EC | Elliptic Compactness |
| FFT | Fast Fourier Transform |
| GLCM | Gray-Level Co-Occurrence Matrix |
| GLDM | Gray-Level Difference Matrix |
| HIPPA | Health Insurance Portability and Accountability Act |
| LTE | Laws Texture Energy |
| PACS | Picture Archiving and Communication System |
| RCC | Renal Cell Carcinoma |
| RD | Radial Distance |
| RF | Random Forest |
| ROC | Receiver Operation Characteristic |
| ROI | Region of Interest |
| SSIGN | Stage, Size, Grade, Necrosis |
| TCGA-KIRC | The Cancer Genome Atlas-Kidney Renal Clear Cell Carcinoma |
| TNM | Tumor-Node-Metastasis |
| VOI | Variable of Importance |
| WHO/ISUP | World Health Organization/International Society of Urological Pathology |
| ZC | Zero-Crossing Count |

Identifying Benign and Malignant Tumors

Various experiments disclosed herein both establish the validity of this approach and demonstrate the effective application of various embodiments of machine learning/artificial intelligence radiomics technology. For instance, in a first scenario, a prospectively-maintained single-institutional renal mass registry was queried to identify patients with a computed tomography-proven clinically-localized renal mass who underwent partial or radical nephrectomy. Radiomic analysis of pre-operative scans was performed. Clinical and radiomic variables of importance were identified through decision tree analysis, which were incorporated into Random Forest and REAL Adaboost predictive models. The primary outcome was the degree of congruity between the virtual diagnosis and final pathology. Subanalyses were performed for small renal masses and patients who had percutaneous renal mass biopsies as part of their workup. Receiver operating characteristic (ROC) curves were used to evaluate the discriminatory function of each model.

In the aforementioned instance, 684 patients met selection criteria. Of these, 76% had renal cell carcinoma; 57% had a small renal mass, of which 73% were malignant. Predictive modeling differentiated benign pathology from malignant with an AUC of 0.84 (95% C.I. 0.79-0.9). In small renal masses, radiomic analysis yielded a discriminatory AUC of 0.77 (95% C.I 0.69-0.85). When negative and non-diagnostic biopsies were supplemented with radiomic analysis, accuracy increased from 83.3% to 93.4%.

Analysis of the example instance provides that radiomic-based predictive modeling distinguishes benign from malignant renal masses. Clinical factors did not substantially improve the diagnostic accuracy of predictive models. Enhanced diagnostic predictability may improve patient selection before surgery and increase the utilization of active surveillance protocols.

Turning in greater detail to the first scenario, a prospectively maintained renal mass database of 1,178 patients who underwent partial or radical nephrectomy from was queried. All patients included in the study had a clinically-localized renal mass identified on multiphase CT scans of the abdomen and pelvis. At minimum, nephrographic and excretory phases were required for study inclusion. Patients with lipid-rich angiomyolipomas, identified by the presence of macroscopic fat on CT, were excluded from this study. All patients had renal surgery in the form of robotic, laparoscopic, or open partial or radical nephrectomy. Demographic and clinical factors, including age, race, co-morbid conditions, smoking status, family history, and renal function, and tumor-specific variables were evaluated for all study participants. The probability of malignant disease was calculated for all patients with renal tumors<7 cm using a pre-defined clinical nomogram that evaluates probability of malignant disease on using age, gender, local symptoms at diagnosis, smoking status, and renal mass size.

Pre-operative CT scans were obtained in 54% of patients, using a set protocol and scanner (Brilliance 64, Philips Healthcare). Briefly, imaging was captured with the patient performing a breath-hold, using the following parameters: 120 kVp, variable tube current, 0.5 mm slice thickness, and 2 mm reconstruction interval. An unenhanced CT scan of the abdomen was obtained first, followed by corticomedullary (30 seconds), nephrographic (90 seconds), and excretory (5-7 minutes) phase scans. Approximately 100-150 mL of nonionic water-soluble intravenous iodinated contrast medium (iopamidol, Isovue 350, Bracco Imaging) dosed to weight was administered with a power injector at a rate of 5 mL/sec. 46% of patients obtained their multiphase imaging at an outside institution, and these were uploaded onto the picture archiving and communication system. In patients with multiple CT scans, the scan immediately preceding surgery was used.

Using Synapse software (FujiFilm, Stamford CT), tumors were segmented as volumes of interest. The nephrographic phase most commonly provided the clearest tumor delineation and was used as the reference template for co-registration in other phases. Images were co-registered by means of normalized mutual information cost function implemented in the Statistical Parametric Mapping software package (Wellcome Trust Centre for Neuroimaging, UK). Custom Matlab (MathWorks®, Natick, MA) code was used to extract voxel data corresponding to the volume of interest. Two-dimensional shape and texture analysis were performed on the largest tumor diameter within each imaging plane, and three-dimensional shape and texture analyses were conducted on the entire tumor volume.

Various machine learning techniques were implemented. For instance, Random Forest (SAS HPFOREST) and REAL Adaboost (SAS % Adaboost) platforms were used to build the prediction model. For Random Forest, 800 trees were used. Average Square Error plots were used to select the optimal numbers of decision trees, variables for each tree-building, and the leaf size of the tree. 60% of original observations were used to bootstrap each tree. The maximal depth of each tree was set to 50. 10% of data were reserved as the independent testing sample. As REAL Adaboost is a more efficient platform, only 25 trees were built with a depth of five and a learning rate of 0.2, as previously recommended. The Loh method was used for variable selection. VOIs were identified using an out-of-bag error GINI index. Rather than a single split learning and testing set, a 90% versus 10% validation procedure was repeated 10 times, with 10 mutually exclusive, 10% testing datasets (10-fold cross-validation). Important features ranking was generated based on the frequency with which that feature appeared in the top 20 for each of the 90% learning versus 10% testing procedures (re-iterated 10 times for robust classification accuracy). This method is less prone to biases that could result from differences in image acquisition. 10-fold cross validation has been substantiated through simulation studies that show that when total sample size exceeds 200, subset models behave like the full learning model. VOIs were then incorporated into the decision tree analysis model, to identify a best fit equation to predict malignant disease.

AUC from ROC curves were used to assess model performance. The analysis compared the AUC of the full model (radiomic features+clinical factors) with reduced models (either radiomic features or clinical factors alone) using a Z-test. SAS software (version 9.4, SAS Institute) was used for all statistical analyses.

Figure 2:
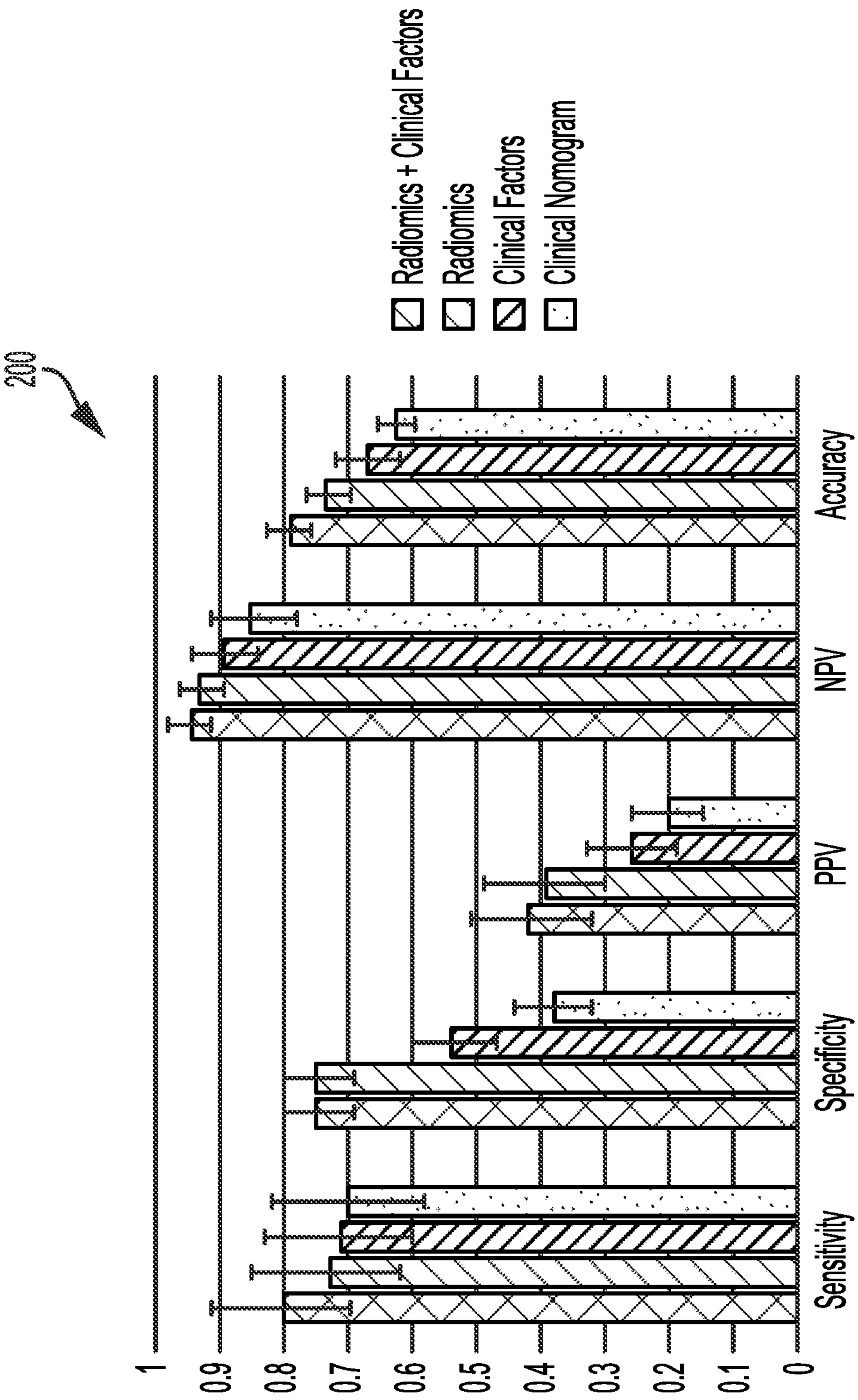
FIG. 2 shows a confusion matrix for radiomic and clinical factors, in accordance with various embodiments.

The first scenario produced results as follows. A total of 684 patients with a renal mass confirmed on CT imaging underwent radical or partial nephrectomy and had an established final pathological diagnosis. 521 (76.2%) patients harbored true cancers, in the form of clear cell (77.0%), papillary (14.0%), chromophobe (8.1%), sarcomatoid (0.6%), or unclassified (0.3%) RCC. The remaining 163 (23.8%) patients had benign oncocytomas or lipid-poor angiomyolipomas. FIG. 2 provides a chart 200 that stratifies pathological subtypes that were encountered and provides tumor-specific characteristics. Specifically, FIG. 2 provides a confusion matrix 200 for radiomic and clinical factors. The combination of radiomic analysis using computed tomographic texture analysis and clinical factors yielded a highest sensitivity, specificity, positive predictive value (PPV), negative predictive value (NPV), and accuracy.

Demographic and clinical characteristics are detailed in Table 1. 468 (68.4%) patients with renal masses were male. 257 (37.6%) patients were symptomatic on presentation. There was a family history of renal malignancy in 23 patients (3.4%). The probability of malignant disease on the basis of clinical nomogram yielded scores that ranged from 52.5-96.8. When a value of 75 was set as the cutoff on the basis of sensitivity and specificity profiles (≥75 favoring a diagnosis of RCC; <75 considered equivocal), the clinical nomogram was concordant with a pathological diagnosis of RCC in 75.8% of cases and had an overall diagnostic accuracy of 66.2%.

In the first table, Table 1, example patient demographic and clinical characteristics are shown. Various abbreviations are used with PPY meaning packs per year, and eGFR meaning estimated glomerular filtration rate.

TABLE 1

| | Renal cell carcinoma (n = 521) | Benign renal masses (n = 163) | p-value |
|---|---|---|---|
| Age (median, range) | 62, 23-94 | 63, 17-92 | 0.34 |
| Gender (n, %) | | | <0.001 |
| Female | 141, 27.1 | 74, 45.4 | |
| Male | 379, 72.7 | 89, 54.6 | |
| Ethnicity (n, %) | | | 0.006 |
| White | 353, 67.8 | 115, 70.6 | |
| Black | 31, 6 | 9, 5.5 | |
| Latino | 85, 16.3 | 13, 8 | |
| Asian | 39, 7.5 | 15, 9.2 | |
| Other | 9, 1.7 | 10, 6.1 | |
| Diabetes (n, %) | 120, 23 | 16, 9.8 | <0.001 |
| Hypertension (n, %) | 319, 61.2 | 84, 51.5 | 0.022 |
| Smoking | | | 0.048 |
| Never (n, %) | 310, 59.5 | 113, 69.3 | |
| Current/Former (n, %) | 199, 38.2 | 49, 30.1 | |
| PPY (avg ± S.D.) | 25.2 ± 17.6 | 4 ± 10 | <0.001 |
| Unknown (n, %) | 12, 2.3 | 1, 0.6 | |
| Family History, RCC (n, %) | 17, 3.3 | 6, 3.7 | 0.046 |
| Family History, other malignancy (n, %) | 164, 31.5 | 30, 18.4 | <0.001 |
| Creatinine (avg ± S.D.) | 1.1 ± 0.9 | 1 ± 1 | 0.35 |
| eGFR (avg ± S.D.) | 76.5 ± 25.8 | 83.7 ± 25.8 | 0.002 |
| Prior biopsy (n, %) | 53, 10.2 | 8, 4.9 | 0.057 |
| Laterality (n, %) | | | 0.10 |
| Left | 249, 47.8 | 76, 46.6 | |
| Right | 270, 51.8 | 77, 47.2 | |
| Bilateral | 0, 0 | 0, 0 | |
| Tumor size (n, %) | | | 0.083 |
| <4 cm | 284, 54.5 | 106, 65.0 | |
| 4 to <7 cm | 149, 28.6 | 32, 19.6 | |
| 7 to <10 cm | 48, 9.2 | 12, 7.4 | |
| ≥10 cm | 40, 7.7 | 13, 8.0 | |
| Clinical presentation (n, %) | | | 0.248 |
| Asymptomatic | 349, 67 | 108, 66.3 | |
| Abdominal/flank pain | 91, 17.5 | 37, 22.7 | |
| Abdominal/flank mass | 6, 1.2 | 0, 0 | |
| Hematuria | 87, 16.7 | 21, 12.9 | |
| Fatigue | 6, 1.2 | 0, 0 | |
| Weight loss | 5, 0.9 | 1, 0.6 | |
| Pathological fracture | 3, 0.6 | 0, 0 | |

Rate ratios of clinical and radiomic based factors in differentiating benign from malignant disease are provided in Tables 2 and 3. Table 2 shows rates of developing oncocytoma.

TABLE 2

| Univariable Analysis | | |
|---|---|---|
| Variable | Rate Ratio | 95% C.I. |
| Age (years) | | |
| ≥65 (ref <65) | 1.74 | 1.17-2.57 |
| Ethnicity | | |
| Non-white (ref White) | 0.77 | 0.49-1.21 |
| BMI | | |
| ≥30 (ref <30) | 0.94 | 0.63-1.41 |
| Smoking status | | |
| Current or former (ref No) | 0.87 | 0.58-1.32 |
| Creatinine (mg/dL) | | |
| ≥1.5 (ref <1.5) | 0.84 | 0.39-1.81 |
| eGFR (mL/min) | | |
| 60-89 (ref ≥90) | 1.56 | 0.56-4.25 |
| 30-59 (ref ≥90) | 1.54 | 0.52-4.42 |
| 15-29 (ref ≥90) | 1.53 | 0.34-6.7 |
| <15 (ref ≥90) | 1.07 | 0.34-2.84 |
| Diabetes mellitus (ref No) | 0.45 | 0.25-0.81 |
| Hypertension (ref No) | 0.89 | 0.6-1.31 |
| Family history, RCC (ref No) | 1.31 | 0.48-3.55 |
| Family history, other cancer (ref No) | 0.32 | 0.18-0.59 |
| Laterality | | |
| Right (ref Left) | 1.0 | 0.68-1.47 |
| Symptomatic (ref No) | NA | NA |
| Clinical nomogram (%) | | |
| 50-59 | | |
| 60-69 | | |
| 70-79 (ref <70) | 1.57 | 0.95-2.58 |
| 80-89 (ref <70) | 1.06 | 0.64-1.77 |
| >90 (ref <70) | 0.49 | 0.22-1.07 |
| Radiomic score (%) | | |
| 50-59 (ref ≥90) | 16.54 | 2.18-125.2 |
| 60-69 (ref ≥90) | 15.05 | 2.06-109.85 |
| 70-79 (ref ≥90) | 8.54 | 1.16-62.7 |
| 80-89 (ref ≥90) | 5.9 | 0.8-43.69 |

Table 3 shows rates of developing RCC.

TABLE 3

| Univariable Analysis | | |
|---|---|---|
| Variable | Rate Ratio | 95% C.I. |
| Age (years) | | |
| ≥65 (ref <65) | 0.87 | 0.71-1.06 |
| Ethnicity | | |
| Non-white (ref White) | 1.06 | 0.86-1.32 |
| BMI | | |
| ≥40 (ref <40) | 1.24 | 0.87-1.77 |
| Smoking status | | |
| Current or former (ref No) | 1.04 | 0.84-1.27 |
| Creatinine (mg/dL) | | |
| ≥1.5 (ref <1.5) | 1.04 | 0.73-1.49 |
| eGFR (mL/min) | | |
| 60-89 (ref ≥90) | 0.9 | 0.58-1.41 |
| 30-59 (ref ≥90) | 0.91 | 0.56-1.46 |
| 15-29 (ref ≥90) | 0.91 | 0.43-1.92 |
| <15 (ref ≥90) | 1.0 | 0.64-1.58 |

TABLE 3-continued

| Univariable Analysis | | |
|---|---|---|
| Variable | Rate Ratio | 95% C.I. |
| Diabetes mellitus (ref No) | 1.17 | 0.94-1.46 |
| Hypertension (ref No) | 1.03 | 0.84-1.26 |
| Family history, RCC (ref No) | 0.92 | 0.51-1.68 |
| Family history, other cancer (ref No) | 1.23 | 1.0-1.52 |
| Laterality | | |
| Right (ref Left) | 1.0 | 0.82-1.22 |
| Symptomatic (ref No) | 1.04 | 0.84-1.27 |
| Clinical nomogram (%) | | |
| 50-59 | | |
| 60-69 | | |
| 70-79 (ref <70) | 1.57 | 0.95-2.58 |
| 80-89 (ref <70) | 1.06 | 0.64-1.77 |
| >90 (ref <70) | 0.49 | 0.22-1.07 |
| Radiomic score (%) | | |
| 50-59 (ref ≥90) | 16.54 | 2.18-125.2 |
| 60-69 (ref ≥90) | 15.05 | 2.06-109.85 |
| 70-79 (ref ≥90) | 8.54 | 1.16-62.7 |
| 80-89 (ref ≥90) | 5.9 | 0.8-43.69 |

Univariate analyses were performed to explore the association between clinical and radiographic features and final pathology. All clinical datapoints, including the above-described clinical nomogram, and the radiomic-based probability of malignancy were incorporated. Age, male gender, smoking history, comorbid diabetes or hypertension, morbid obesity, symptomatic presentation, very high clinical nomogram score (≥90), and malignancy suspected on the basis of radiomic analysis were significant variables. Family history of RCC, baseline creatinine, comorbid chronic kidney disease, and laterality were non-significant variables. As mentioned, FIG. 2 shows a confusion matrix 200 for clinical and radiomic factors. The addition of clinical factors to radiomic analysis improved the sensitivity from 0.73 to 0.8, and the negative predictive value of the combined features was 0.94 (C.I. 0.91-0.98).

Figure 3B:
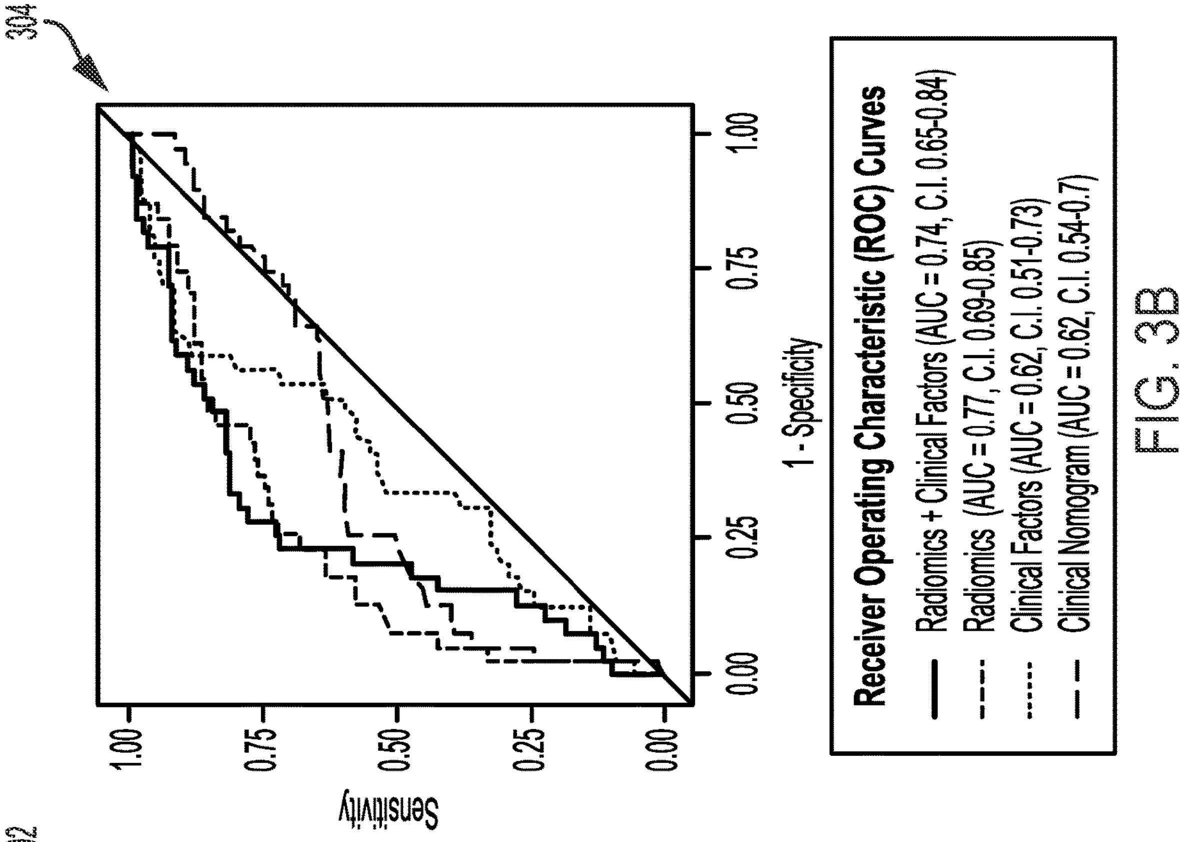
FIGS. 3A-B show a first set and second set of receiver operating characteristics (ROC) curves, in accordance with various embodiments.
Figure 3A:
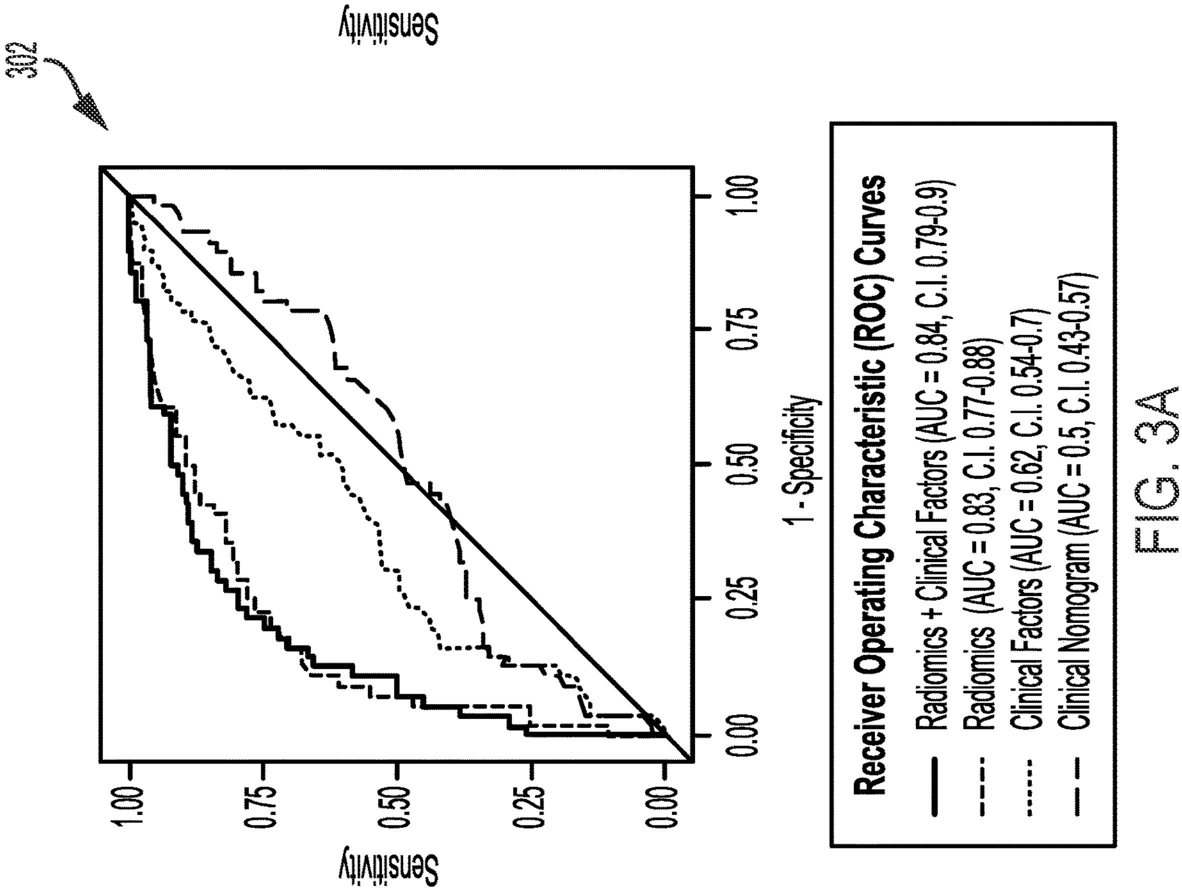

Turning to FIGS. 3A-B, a first set 302 and a second set 304 of receiver operating characteristics (ROC) curves are shown. These curves illustrate that the REAL Adaboost model had the best predictive performance as demonstrated by ROC curves to evaluate the strength of clinical and radiomic factors in distinguishing benign disease from malignancy. With reference to the first set 302 of ROC curves, clinical factors alone performed with an AUC of 0.62 (95% C.I. 0.54-0.7), and radiomic analysis alone was able to predict true malignancy with an AUC of 0.83 (C.I. 0.77-0.88). Of note, the clinical nomogram model was equivocal in its predictive capacity, with an AUC of 0.5 (C.I. 0.43-0.57). The competency of the analysis to distinguish benign from malignant disease was highest when radiomic and clinical features were combined (AUC=0.84, 95% C.I. 0.79-0.9).

A sensitivity analysis was performed for patients with SRMs, defined as less than 4 cm (n=390, 57.0%). Of these, 106 (27.2%) and 284 (72.8%) patients had benign disease and RCC on final pathology, respectively. With reference to the second set 304 of ROC curves, in the setting of an SRM, radiomic analysis was able to differentiate benign disease from RCC with an AUC of 0.77 (C.I. 0.69-0.85). The addition of clinical factors to the radiomic evaluation did not significantly alter the predictive capacity of the model.

A sensitivity analysis was performed to evaluate the concordance of percutaneous biopsy and radiomic analysis with final pathology. A total of 61 (8.8%) patients underwent RMB before surgery. Specificity was 100%. RMBs were non-diagnostic in 8.3% and falsely benign in an additional 8.3% of patients. Of the patients who were misclassified on the basis of RMB, 60% were correctly diagnosed through radiomic analysis alone (See Table 4). When benign and non-diagnostic biopsy pathologies were supplemented with radiomic findings, the sensitivity increased from 81.1% to 92.5% and the accuracy from 83.3% to 93.4%.

TABLE 4

| RENAL MASS BIOPSY | VIRTUAL BIOPSY | FINAL PATHOLOGY |
|---|---|---|
| Malignant | Malignant | Clear cell RCC |
| Malignant | Malignant | Clear cell RCC |
| Malignant | Malignant | Clear cell RCC |
| Non-diagnostic | Malignant | Clear cell RCC |
| Malignant | Malignant | Clear cell RCC |
| Malignant | Malignant | Clear cell RCC |
| Benign | Malignant | Clear cell RCC |
| Malignant | Malignant | Clear cell RCC |
| Malignant | Malignant | Clear cell RCC |
| Malignant | Malignant | Clear cell RCC |
| Benign | Benign | Clear cell RCC |
| Malignant | Malignant | Clear cell RCC |
| Non-diagnostic | Non-diagnostic | Clear cell RCC |
| Non-diagnostic | Non-diagnostic | Clear cell RCC |
| Malignant | Malignant | Clear cell RCC |
| Malignant | Malignant | Clear cell RCC |
| Malignant | Malignant | Clear cell RCC |
| Malignant | Malignant | Clear cell RCC |
| Malignant | Malignant | Clear cell RCC |
| Malignant | Malignant | Clear cell RCC |
| Malignant | Malignant | Clear cell RCC |
| Malignant | Malignant | Clear cell RCC |
| Malignant | Malignant | Clear cell RCC |
| Malignant | Malignant | Clear cell RCC |
| Malignant | Malignant | Clear cell RCC |
| Malignant | Malignant | Clear cell RCC |
| Malignant | Malignant | Clear cell RCC |
| Benign | Malignant | Clear cell RCC |
| Malignant | Malignant | Clear cell RCC |
| Malignant | Malignant | Clear cell RCC |
| Malignant | Malignant | Clear cell RCC |
| Non-diagnostic | Malignant | Clear cell RCC |
| Malignant | Malignant | Clear cell RCC |
| Malignant | Malignant | Clear cell RCC |
| Non-diagnostic | Malignant | Clear cell RCC |
| Malignant | Malignant | Clear cell RCC |
| Malignant | Malignant | Clear cell RCC |
| Malignant | Malignant | Clear cell RCC |
| Benign | Malignant | Clear cell RCC |
| Malignant | Malignant | Clear cell RCC |
| Malignant | Malignant | Clear cell RCC |
| Malignant | Malignant | Clear cell RCC |
| Malignant | Malignant | Clear cell RCC |
| Malignant | Malignant | Clear cell RCC |
| Malignant | Malignant | Papillary RCC |
| Malignant | Malignant | Papillary RCC |
| Malignant | Malignant | Papillary RCC |
| Benign | Benign | Papillary RCC |
| Malignant | Malignant | Papillary RCC |
| Malignant | Malignant | Papillary RCC |
| Malignant | Malignant | Chromophobe RCC |
| Malignant | Malignant | Sarcomatoid RCC |
| Malignant | Malignant | Sarcomatoid RCC |

TABLE 4-continued

| RENAL MASS BIOPSY | VIRTUAL BIOPSY | FINAL PATHOLOGY |
|---|---|---|
| Benign | Benign | Oncocytoma |
| Benign | Benign | Oncocytoma |
| Benign | Benign | Oncocytoma |
| Benign | Benign | Oncocytoma |
| Benign | Benign | Oncocytoma |
| Non-diagnostic | Benign | Angiomyolipoma |
| Benign | Benign | Angiomyolipoma |
| Benign | Benign | Angiomyolipoma |

A machine-learning predictive model incorporates clinical and radiomic VOIs discriminated benign renal masses from RCC with an AUC of 0.84 (95% C.I. 0.79-0.9). Augmenting negative and non-diagnostic biopsy pathology with radiomics-based predictive modeling substantially improved the sensitivity and accuracy of RMBs to 92.5% and 93.5%. Clinical factors, either individually or in the context of a clinical nomogram were weakly predictive and did not improve the diagnostic yield of the model. In the context of SRMs, radiomic analysis alone offered the highest diagnostic yield.

The incidentally detected renal mass represents a heterogenous group of potential tumors. Precise evaluation of malignant potential should be performed before patients undergo treatment. Radiomic analysis of cross-sectional imaging is a non-invasive tool that may be able to differentiate benign from malignant disease and also differentiate between tumor subtypes. Approximately 25% of the patients in this study ultimately had benign disease after surgical resection, consistent with reported findings of benign pathology in up to 30% of patients. Though some larger tumors were removed because of symptoms and mass effect, 15% of patients (106/684) in the surgical series had oncocytomas or angiomyolipomas<4 cm. A safe assumption can be made that these masses were removed unnecessarily. While non-treatment of confirmed cancers would be concerning, equally, overtreatment of SRMs yields an unknown survival benefit and can expose patients to psycho-social stressors, peri-operative complications, reduced renal function, and introduces financial toxicities. In this cohort, had surgical intervention been based on the combination of clinical and radiomic predictors of malignant disease, the number of unnecessary surgeries could have dropped to 3.5%, reducing unnecessary surgical intervention rate four-fold.

Clinical factors, even those identified as significant on univariable analysis, had lower capacity for distinguishing benign from malignant pathology. The addition of clinical VOIs to the radiomic analysis raised the overall AUC by only 0.01, suggesting that clinical factors alone might be best considered when incorporated into a broader framework that is based on radiomic analysis. In patients with SRMs, clinical factors did not add a diagnostic benefit to the predictive model. In this setting, radiomic analysis provided the greatest predictive capacity (AUC 0.77).

Two subsets of patients in particular are most likely to benefit from improved pre-surgical risk stratification. The first is the patient with an asymptomatic SRM. Current data support the oncological safety of AS in the well-selected patient, with serial imaging obtained at 6-12 month intervals to evaluate for changes in tumor architecture and size. While CT or MRI are preferred because of improved resolution and reproducibility, radiation exposure and practical considerations, including scanner availability and insurance authorization, serve as potential barriers to CT or MRI-based AS. Furthermore, the financial costs of serial cross-sectional imaging should be considered. Improved risk stratification offered through radiomic analysis may allow for an increased interval of time between imaging and/or increased utilization of ultrasound as a safer and cheaper imaging AS modality.

The second subset of patient to benefit from radiomic analysis is the poor surgical candidate. Patients with multiple co-morbidities and shorter life expectancy have an increased risk of peri-operative complications, and every effort should be made to safely avoid surgical intervention. A potential implication of radiomics is an expansion of the pool of patients eligible for AS. Though typically limited to patients with SRMs, the infirm patient with an asymptomatic renal mass larger than 4 cm but with a very low probability of malignancy on radiomic analysis could be more justifiably considered for AS. In such a setting, if radiomic analysis suggests a low probability of malignancy, and RMB is also benign or non-diagnostic, our data indicate that close AS could be an option. Such cases should be considered on an individual basis, with an in-depth discussion between physician and patient about the risks for false negative findings on RMB and the increased risk of metastatic potential when masses exceed 4 cm.

Aside from radiomics, molecular imaging using radionuclide tagged probes detected with positron emitted tomography or single photon emission computed tomography has also shown promising results in allowing for presurgical evaluation of malignant potential. A benefit of radiomics over molecular imaging is that no additional imaging is required beyond the baseline contrast-enhanced CT scan that the majority of patients obtain as part of guideline-recommended workup. Radiomic evaluation disclosed herein is, in various embodiments, using variables with low inter-user variability in an effort to maximize the translatability and reproducibility of these findings across different institutions, irrespective of center-to-center differences in imaging protocols.

The utility of RMB is limited by patient factors, tumor location and non-diagnostic potential. Reported sensitivities and specificities range from 80-92% and 83-100%. Generally, SRMs have higher false negative rates, with a low reported negative predictive value of 60%. Furthermore, benign biopsy histology cannot rule out malignancy in the rest of the tumor, particularly in chromophobe varieties. A definitive benign diagnosis may be inferred from RMB when pathology is consistent with angiomyolipoma, metanephric adenoma, or focal infection. A biopsy specimen showing nondiagnostic or nonmalignant findings must be considered with caution, and surveillance imaging, repeat biopsy, or surgery is currently recommended. In above example scenarios, RMB specificity was 100%, but sensitivity and accuracy were 81% and 83%, respectively. Adjudication of benign and non-diagnostic pathology with radiomic analysis increased the sensitivity and accuracy to 92.5% and 93.4%. Of note, patients in this series with benign pathology on RMB ultimately underwent renal surgery because of persistent symptoms and concern for malignancy.

Though a CT study with contrast is the most common cross-sectional imaging modality used, not all patients can safely receive contrast. The present study is limited to patients with at least nephrographic and excretory phased CT imaging. Though the retrospective nature of the analysis could be considered a limitation of this study, all data were collected and maintained prospectively. Beyond the context of a clinical trial, in which patient management might change on the results, a prospective analysis is not expected to strengthen the validity of the study, which reports on a machine-learning platform's ability to predict final pathology. While other studies use single-split learning and testing sets, this disclosure employed 10-fold cross-validation to more efficiently eliminate biases that could results from differences in scanners and image acquisition protocols. A limitation in all machine-learning radiomic-based studies to date is the absence of a widely adopted protocol. Until such radiomic algorithms are established, variability amongst centers will persist. The AI platform for radiomic analysis is strengthened by the number of patients, and while the present study represents the largest study to date of its kind, future studies with a greater number of patients and multiple institutions would further validate the utility of this platform. Moreover, the natural incidence of non-clear cell renal malignancy is low. In the experiment, the incidence of hereditary diseases that would predispose patients to renal malignancy was 1%. A larger cohort of patients would allow evaluation of whether radiomic and clinical factors can reliably differentiate between different subtypes of RCC. Lastly, the surgical nature of this series of patients has inherent limitations; namely, patients with benign pathology on RMB still underwent surgery for persistent symptoms or concerns for malignancy. Benign findings on RMB in a patient with low concern for malignancy may obviate the need for surgery, but these patients were not included in this study.

The harms of overtreatment of renal masses include psychosocial patient distress, surgical complications, impaired kidney function, unknown survival benefit, and financial toxicity. Radiomic analysis may improve preoperative risk stratification, and as a result, mitigate some of these harms. If implemented broadly, the enhanced diagnostic predictability of radiomic platforms increase the utility of AS protocols and help avoid surgery in patients who are at high risk for peri-operative complication.

A machine-learning predictive model that incorporates radiomic analysis may distinguish benign pathology from RCC, without the need for adjunctive imaging or procedures and within the context of guideline recommended workup. Clinical factors are weakly predictive and their incorporation into a radiomic-based predictive model is not needed to obtain significant diagnostic yield.

Stratifying Tumor Grade and Stage

Machine learning augmented radiomics analysis can also provide a non-invasive approach to stratify high from low tumor grade as well as high from low tumor-node-metastasis (TNM) stage. According to the American Cancer Society, kidney cancer will be responsible for approximately 76,080 new cases and 13,780 deaths in 2021, and currently ranks as one of the top 10 most common malignancies in both men and women. The vast majority of malignant kidney tumors are of the renal cell carcinoma (RCC) type, and over three quarters of RCCs fall under the classification of clear cell renal cell carcinoma (ccRCC). Computed tomography (CT), particularly multiphase contrast-enhanced CT (CECT), is the most commonly utilized imaging technique for investigation of renal masses due to its substantial accuracy for both detection and staging. Yet, current clinical decision-making schemas for ccRCC still remain heavily reliant on subjective histopathological assessment and notably do not incorporate the use of quantitative imaging biomarkers.

Radiomics analyses rely on the algorithmic extraction of quantitative features of the grayscale in medical images to construct high-dimensional datasets. Although still a growing area of research, radiomics has revealed its potential to support oncological care through applications in computer-aided diagnosis and detection of cancer. Radiomics-based computer-aided prediction models similarly hold substantial promise to augment existing prediction and prognostication algorithms for ccRCC through objective and comprehensive phenotypic characterization schemas. Currently, poor standardization and generalization has hindered the clinical translation of radiomics workflows to patient care settings.

In recent years, assignment of RCC grade has typically been done by the World Health Organization and International Society of Urological Pathology (WHO/ISUP) grading system. This system, involving assessment of nucleolar characteristics, was developed in 2012 to address several limitations found in other RCC classification systems, for example, the Fuhrman grading system. Though it has demonstrated superiority in predicting clinical outcomes compared to its predecessors, the current WHO/ISUP grading system requires invasive tissue biopsy and is susceptible to sampling and interobserver errors. In prior efforts, the subjectivity causes pervasive uncertainty in the degree of nucleolar prominence that necessitates a higher grade. In addition, most of the respondents do not require nucleoli to be eosinophilic despite this being an official WHO/ISUP classification description. Such determinations could have profound implications on clinical management given that higher grade tumors may require radical resection as opposed to nephron-sparing surgery or even active surveillance. Therefore, a non-invasive, objective means to evaluate whole tumor grade will improve clinical management of ccRCC and might even more accurately reflect tumor heterogeneity compared to conventional tissue sampling alone.

Figure 4A:
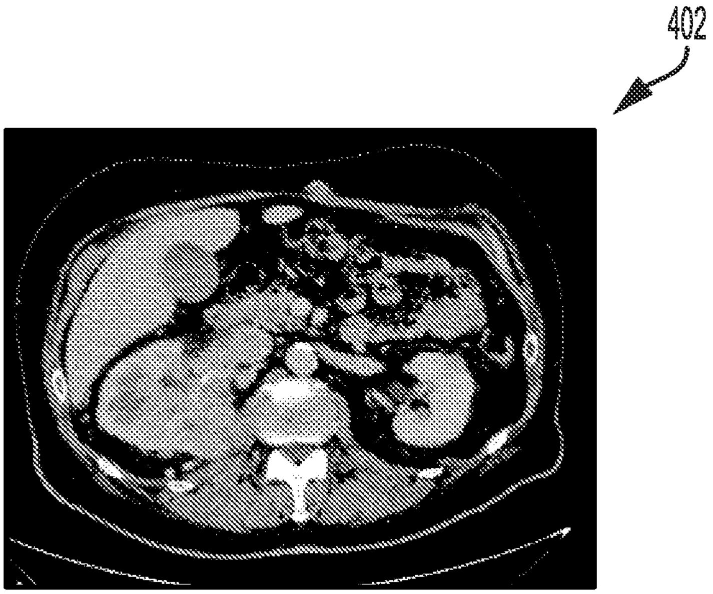
FIGS. 4A-B illustrates example images of kidneys with carcinomas of a high WHO/ISUP grade and TNM stage ccRCC and a low WHO/ISUP grade and TNM stage ccRCC, in accordance with various embodiments.
Figure 4B:
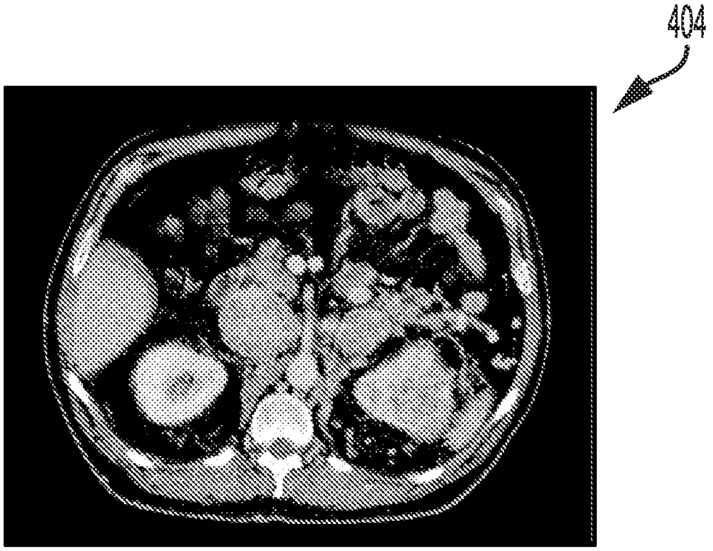

Assignment of stage is generally rendered by standard tumor-node-metastasis (TNM) criteria, which were developed jointly by the Union for International Cancer Control (UICC) and American Joint Committee on Cancer (AJCC). Factors considered in the staging of primary renal malignancies specifically include invasion of the ipsilateral adrenal gland and renal vein in addition to conventional criteria of tumor size, vascular invasion, and locoregional and lymphatic spread. Despite advances in imaging technology, staging of RCCs remains a difficult and imperfect process. Discrimination of stage III from stages I and II is particularly problematic due to challenges identifying important characteristics such as perirenal extension and vascular invasion on conventional tomography. Even among patients with matched tumor stage and grade, inconsistencies in survival outcomes remain. FIGS. 4A-B illustrate an example of a high WHO/ISUP grade and TNM stage ccRCC (FIG. 4A, 402) compared to a low WHO/ISUP grade and TNM stage ccRCC (FIG. 4B, 404). With reference to the illustration 402 of FIG. 4A, an illustration shows kidneys of 65-year-old male with a stage III (T3 N0 M0), WHO/ISUP grade 3 clear cell carcinoma in the right kidney invading into the right renal vein and inferior vena cava on the nephrographic phase. Also of note is a stage II, WHO/ISUP grade 2 clear cell carcinoma in the left kidney. With reference to the illustration 404 of FIG. 4B, an illustration shows kidneys of a 60-year-old male with a stage IV (T4 N1 M1), WHO/ISUP grade 4 clear cell carcinoma in the left kidney. Nephrographic phase axial image illustrates tumor invading the left renal vein and inferior vena cava with metastases to the left adrenal and perinephric extension. Also noted was involvement of paraaortic nodes.

Though there have been many systematic revisions over the years in accordance with emerging knowledge, the TNM staging system for RCC still lacks assimilation of many key prognostic elements. Incorporating additional objective prognostic markers to complement the current staging schema would benefit the care of patients with ccRCC, but unlike the disclosure herein, prior efforts do not leverage machine learning augmented CT-based radiomics analysis to predict TNM stage.

Inclusion criteria for this machine learning augmented CT-based radiomics analysis to predict TNM stage included having a pre-operative single- and multiphase CECT scans of the abdomen and pelvis with complete tumor and kidney visibility, availability of both grade and stage data, and adequate image quality. Retrospective query of a prospectively maintained surgical database consisting of 1178 consecutive radical or partial nephrectomies yielded 401 subjects for possible inclusion in the training cohort. Images and relevant clinical information, including WHO/ISUP grade and TNM stage, were obtained for each potential subject. Four subjects were excluded due to unavailable grade and stage information, thereby resulting in a final training cohort of 397 subjects (mean age 60.1±12.2; range 22-86).

In total, 587 subjects (mean age 60.2 years±12.18; range 22-88.7 years) with histologically confirmed ccRCC were included in the study. Only one primary tumor was segmented for each subject. In cases of multiple tumors, only the dominant tumor was selected. Subjects were divided into a training group (n=397). An external validation sample (n=190) was acquired. For all subjects, "high grade" was defined as tumor grade 3 or 4, whereas "high stage" was defined as TNM stage III or IV. Accordingly, grade 1 or 2 was classified as "low grade" and stage I or II was termed "low stage."

Multiphase CT images, tumor grade, stage, and other relevant demographic information for 209 subjects with ccRCC were downloaded directly from the TCGA-KIRC database. Of these, 16 subjects were excluded due to incomplete kidney or tumor visibility and large slice thickness on imaging. Three additional subjects were excluded after manual segmentation due to incompatibility and subsequent failure in our institutionally developed radiomics pipeline. The remaining 190 subjects (mean age 60.4±12.20; range 26.6-88.7) were utilized for the external validation cohort.

Tumor Segmentation and Radiomics Feature Extraction.

Tumors and whole kidneys were manually segmented slice by slice using Synapse 3D software (Fujifilm Medical Systems, CT). 3D regions of interest (ROIs) of the primary tumor were delineated from surrounding voxels in the nephrographic phase when available. The nephrographic phase was preferred as it provided the best delineation of the tumor and hence was used as the reference target for subsequent co-registration of other phases. Unfortunately, 16 subjects from the training set did not have accompanying nephrographic scans. In order to avoid reducing the sample size by excluding these cases, the analysis instead chose to use other phases of the CECT scans where the lesion was most visible to serve as a template for subsequent co-registration. Complete renal volumes (tumor and affected kidney) were segmented from any remaining CT phases available that satisfied the inclusion criteria.

For both training and validation sets, algorithmic 12 parameter linear 3D co-registration was completed using the Statistical Parametric Mapping (SPM) software in MATLAB®. Overall, 2824 radiomics features across 12 texture families were then extracted in MATLAB® using the custom data processing algorithms in a radiomics pipeline provided below. The radiomics pipeline features 2824 radiomics features across 12 texture families. Texture families spanning first-order metrics such as histogram analysis, second-order metrics (e.g., GLCM and GLDM), and higher order metrics such as DCT, Law Transformation, and Fast Fourier Transform (FFT) were use; GLCM, Gray Level Co-occurrence Matrix; DCT, Discrete Cosine Transform, GLDM, Gray Level Difference Matrix, etc.)

The radiomics panel includes transformation filters (2D and 3D) such as law and FFT. The radiomics panel includes histogram analysis (2D) such as mean, median, skewness, kurtosis, minimum, maximum, quartile, range, and standard deviation. The radiomics panel includes GLCM (2D and 3D) DCT (4 bands) (2D), GLDM (2D and 3D) associated with Haralick metrics. The Haralick metrics include angular second moment, contrast, correlation, dissimilarity, entropy, homogeneity, inverse difference moment mean, IMC 1 and 2 mean, measure of correlation coefficient, mean square root of variance, standard deviation, uniformity, variance, difference average and entropy, sum of average, entropy, and variance, and mean. The radiomics panel includes Grey-level Run Length Matrix (2D and 3D) such as short-run emphasis (RE) long-RE, low-grey RE, high-grey RE, short-run low-grey RE, short-run high-grey RE, long-run low-grey RE, long-run high-grey RE, grey-level non-uniformity, renlength non-uniformity, and run percent. The radiomics panel includes grey-level size zone matrix (2D and 3D) such as small area emphasis, large area emphasis, intensity variability, zone percentage, size zone variance, high intensity emphasis, low intensity emphasis, high intensity small area emphasis, low intensity small area emphasis, high intensity large area emphasis, and low intensity large area emphasis.

Machine Learning and Statistical Analysis.

All statistical analysis was performed using SAS version 9.4 software. Independent t test or Wilcoxon sum rank test with Benjamini and Hochberg Procedure was used for multiple comparisons testing. Models were constructed using (1) all 2824 radiomics features extracted (full model) and (2) 388 previously identified robust features (robust model). The family of robust metrics was shortlisted from the entire radiomics panel based on series of imaging studies conducted using custom-built CT radiomics phantoms scanned on CT scanners from multiple vendors and imaging protocols. Robustness was measured using the interclass correlation two-way-mixed with absolute agreement for single measurement (ICC 3.1) of each of the radiomics metrics across the four CT scanners. Specifically, 60% of features with ICC≥0.70 were deemed robust. The families for the robust features were Intensity, Gray Level Co-Occurrence Matrix (GLCM) 2D and 3D, Gray Level Dependence Matrix (GLDM) 2D and 3D, Gray Level Run Length Matrix (GLRLM) 2D and 3D, and Gray Level Size Zone Matrix (GLSZM) 2D and 3D. Random Forest (RF), Real Adaptive Boosting (Adaboost), and Elastic Net were used to construct the machine learning decision classifiers. During the training phase, a five-fold cross-validation procedure was used to fine tune the machine learning models. Prediction model accuracies were quantitatively evaluated by the area under the curve (AUC) of the receiver operating characteristic (ROC). The out-of-bag Gini index was used to rank variables of importance (VOI).

Interobserver Reliability Assessment and Sensitivity Analysis.

The analysis included conducting an interobserver reliability analysis with three radiologists. As previously reported, each radiologist segmented the tumor margins independently for 15 subjects. Intraclass correlation (ICC) 2-way-mixed with absolute agreement was used to evaluate reliability of the radiomics results, as obtained using a RF classifier, despite the differences in segmentation contours. A sensitivity analysis was conducted with all the three machine learning classifiers for predicting both grade and stage using the robust model and full models.

Figure 5:
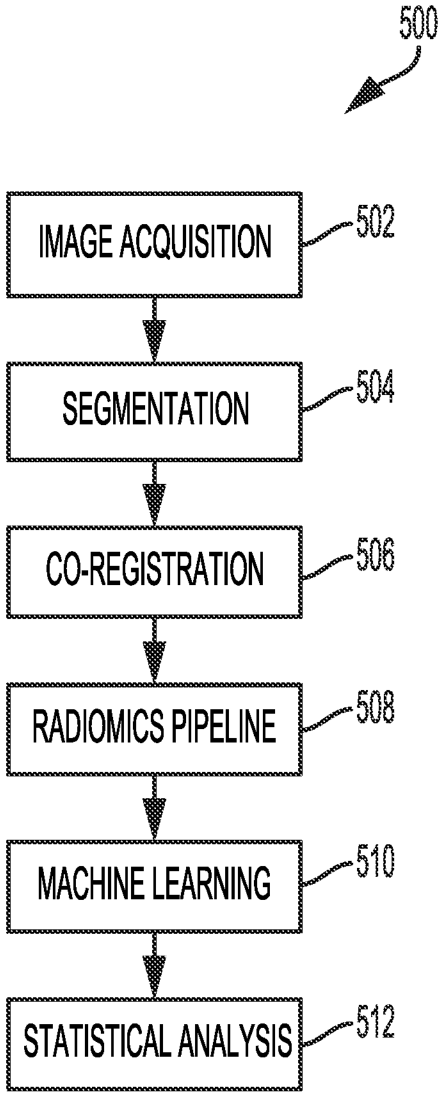
FIG. 5 illustrates a method of radiomics-based machine learning augmented prediction of tumor grade and TNM stage, in accordance with various embodiments.

Referring now to FIG. 5, one may appreciate that a method of radiomics-based machine learning augmented prediction of tumor grade and TNM stage 500 proceeds with a variety of aspects, each according to principles provided herein. The method provides a workflow schema for a process of CT-based radiomics analysis to stratify ccRCC grade and stage. Multiphase CT images from 587 patients with pathologically confirmed ccRCC were manually segmented and co-registered. A total of 2824 radiomics features across 12 texture families were then extracted from the co-registered regions of interest across different CT phases. Three prediction models of ccRCC grade and stage were created and tested using all radiomics features and using only robust radiomics metrics, respectively. As an example, performance assessments for ccRCC stage in the statistical analysis aspect are provided in FIGS. 6A-B.

The method may include image acquisition (block 502). The method may include image segmentation (block 504). The method may include coregistration of the acquired image and the segmentation (block 506). The method may include application of an above described radiomics pipeline (block 508). The method may include application of machine learning (block 510). The machine learning may include application of classifiers. For instance, the classifiers may include one or more of a random forest (RF) classifier, a real adaptive boosting (Adaboost) classifier, an elastic net classifier, and others. The method may include application of statistical analysis (block 512) which will be discussed further herein.

Figure 6A:
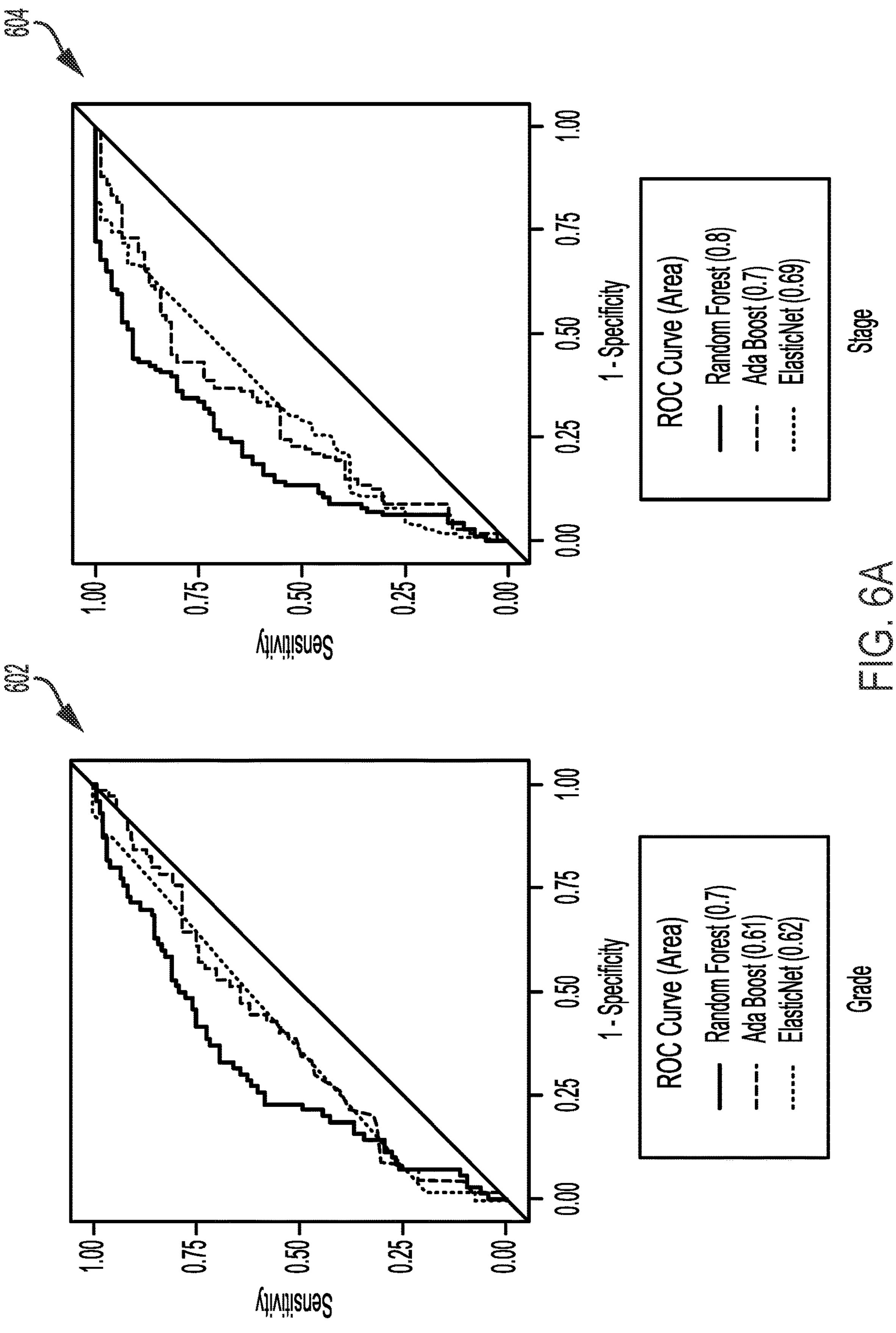
FIGS. 6A-B provide illustrations of receiver operating characteristic (ROC) curves illustrating the prediction accuracies for the stratification of grade and TNM stage in the full model and illustrating the prediction accuracies for the stratification of grade and TNM stage in the reduced robust model, in accordance with various embodiments.
Figure 6B:
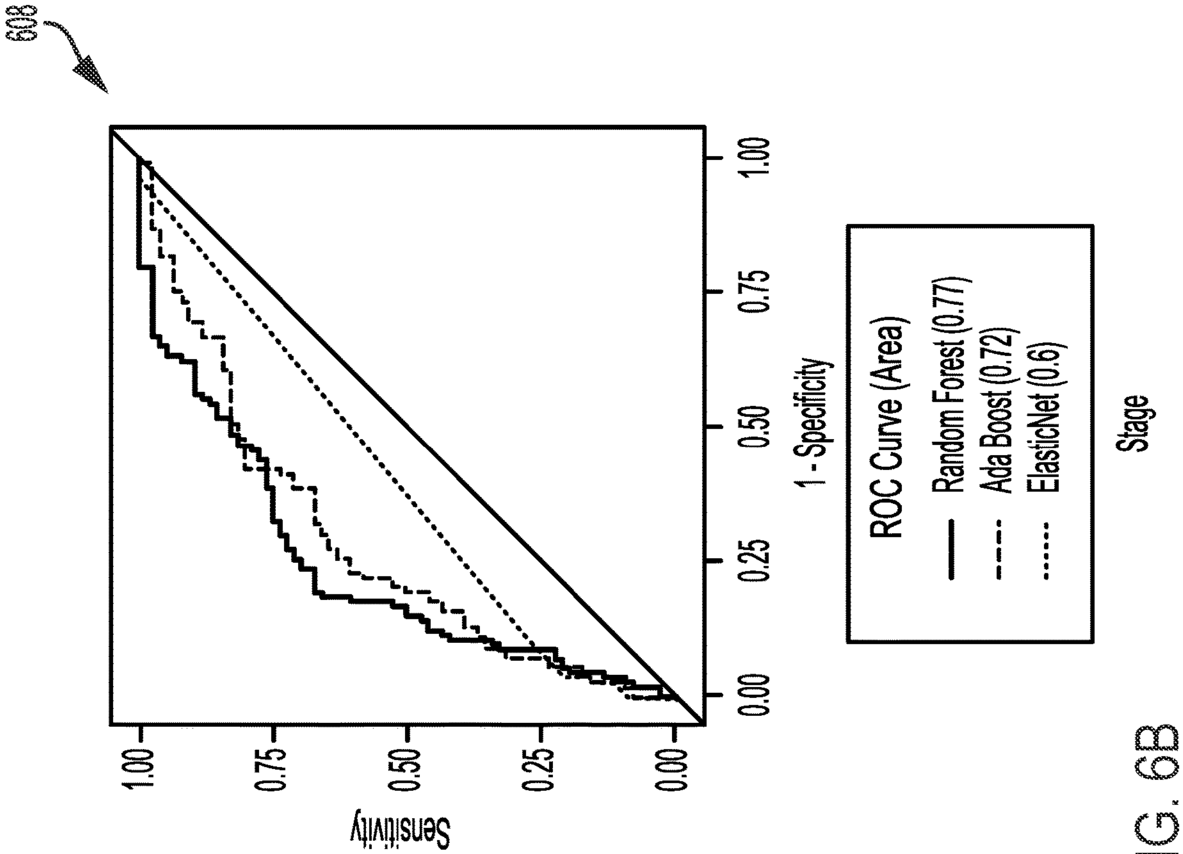
Figure 6B:
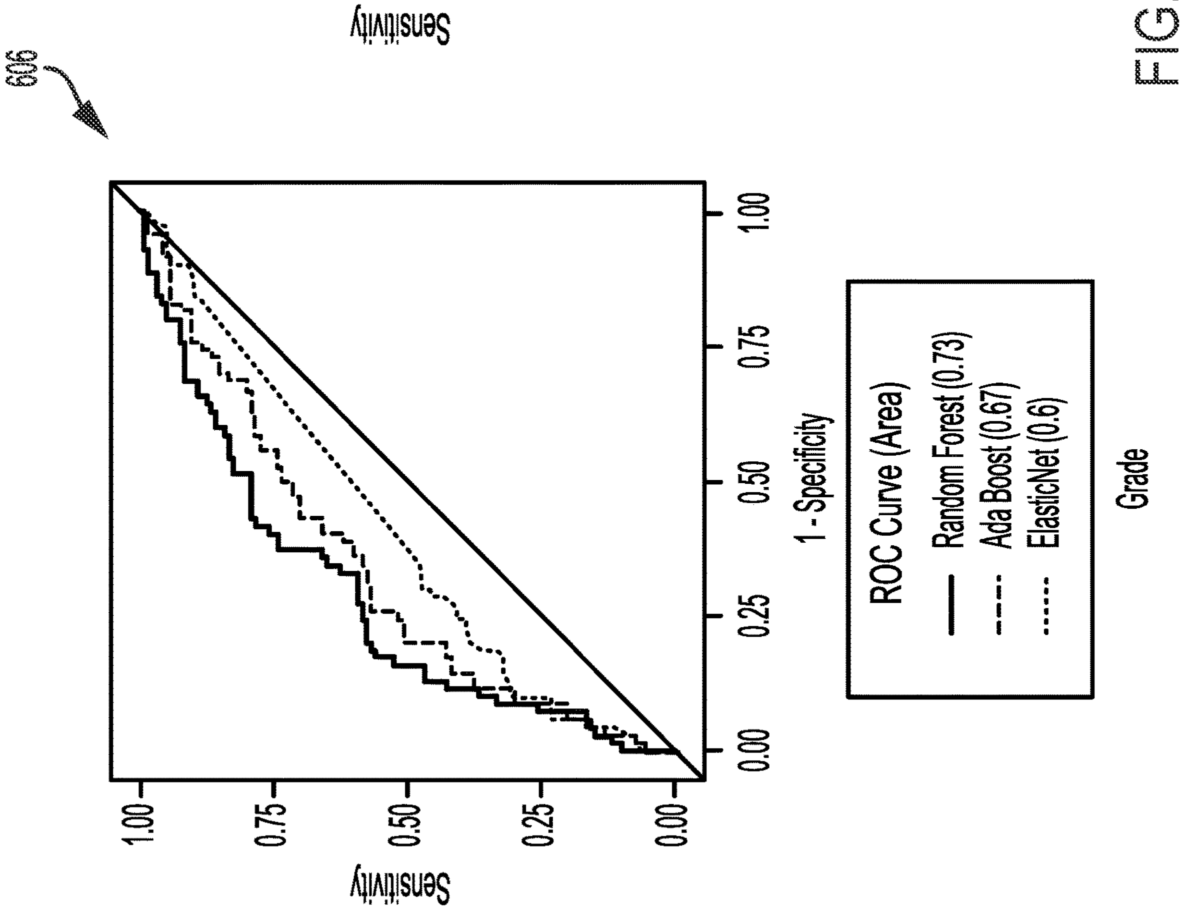

FIGS. 6A-B provide illustrations of receiver operating characteristic (ROC) curves. ROC curves illustrating the prediction accuracies for the stratification of grade 602 and TNM stage 604 in the full model are provided. ROC curves illustrating the prediction accuracies for the stratification of grade 606 and TNM stage 608 in the reduced robust model are provided. AUCs are shown in the legend next to each machine learning classifier (Random Forest, Adaboost, and Elastic Net).

Results.

Full model (all features). ROC curves for prediction of grade and stage are presented in FIG. 6A. AUCs for differentiating high from low tumor grade were 0.70, 0.61, and 0.62 for RF, Adaboost, and Elastic Net, respectively. The AUCs for discriminating high from low TNM stage were 0.80, 0.70, and 0.69 (RF, Adaboost, and Elastic Net, respectively).

Robust model (robust features). ROC curves generated with this robust model for both tumor grade and TNM stage are shown in FIG. 6B. AUCs for differentiating tumor grade were 0.73, 0.67, and 0.60 for RF, Adaboost, and Elastic Net, respectively. For classification of TNM stage, AUCs were 0.77, 0.72, and 0.60 (RF, Adaboost, and Elastic Net, respectively).

Figure 7A:
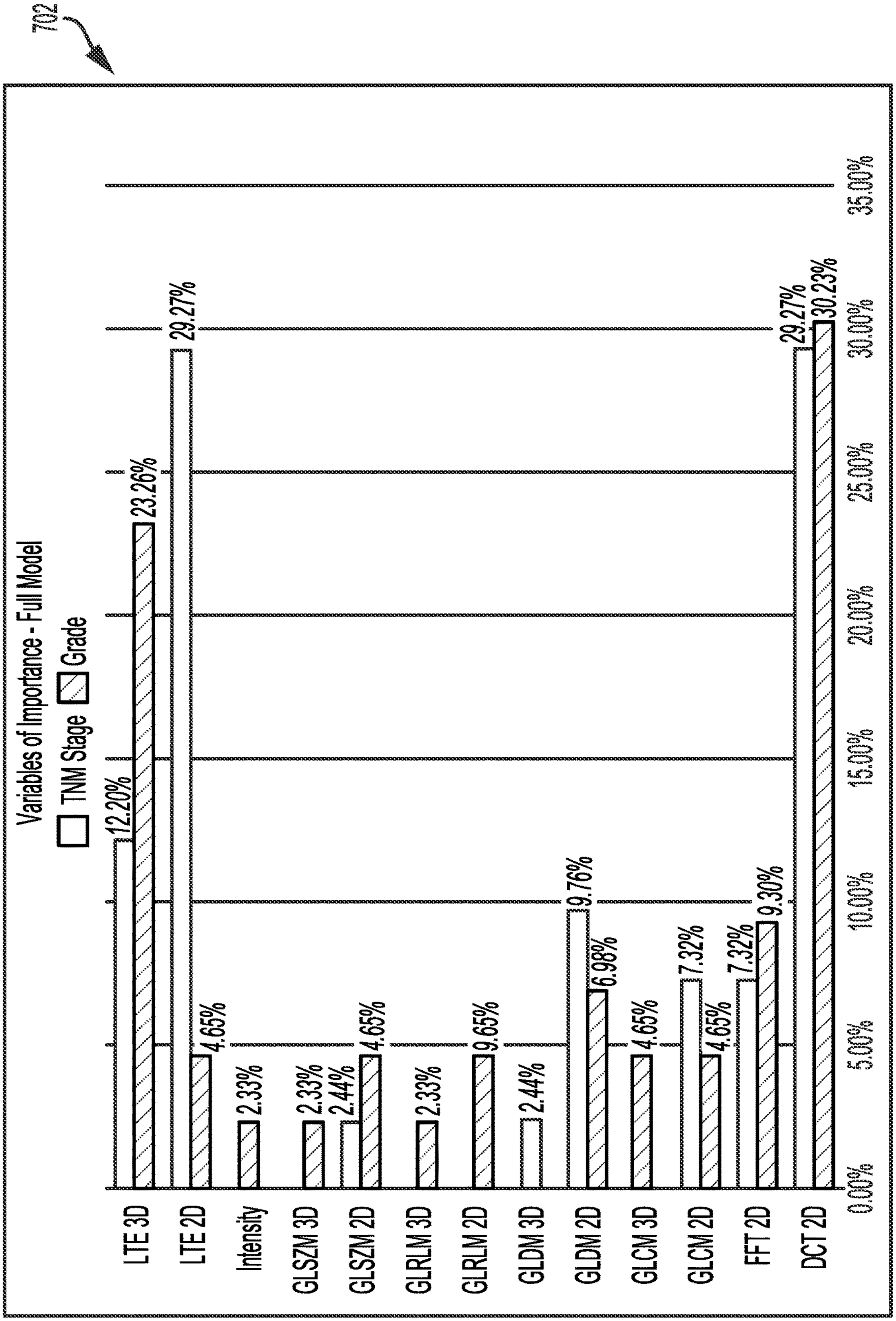
FIG. 7A is a chart illustrating a distribution of VOI across all machine learning classifiers for the full model, in accordance with various embodiments.
Figure 7B:
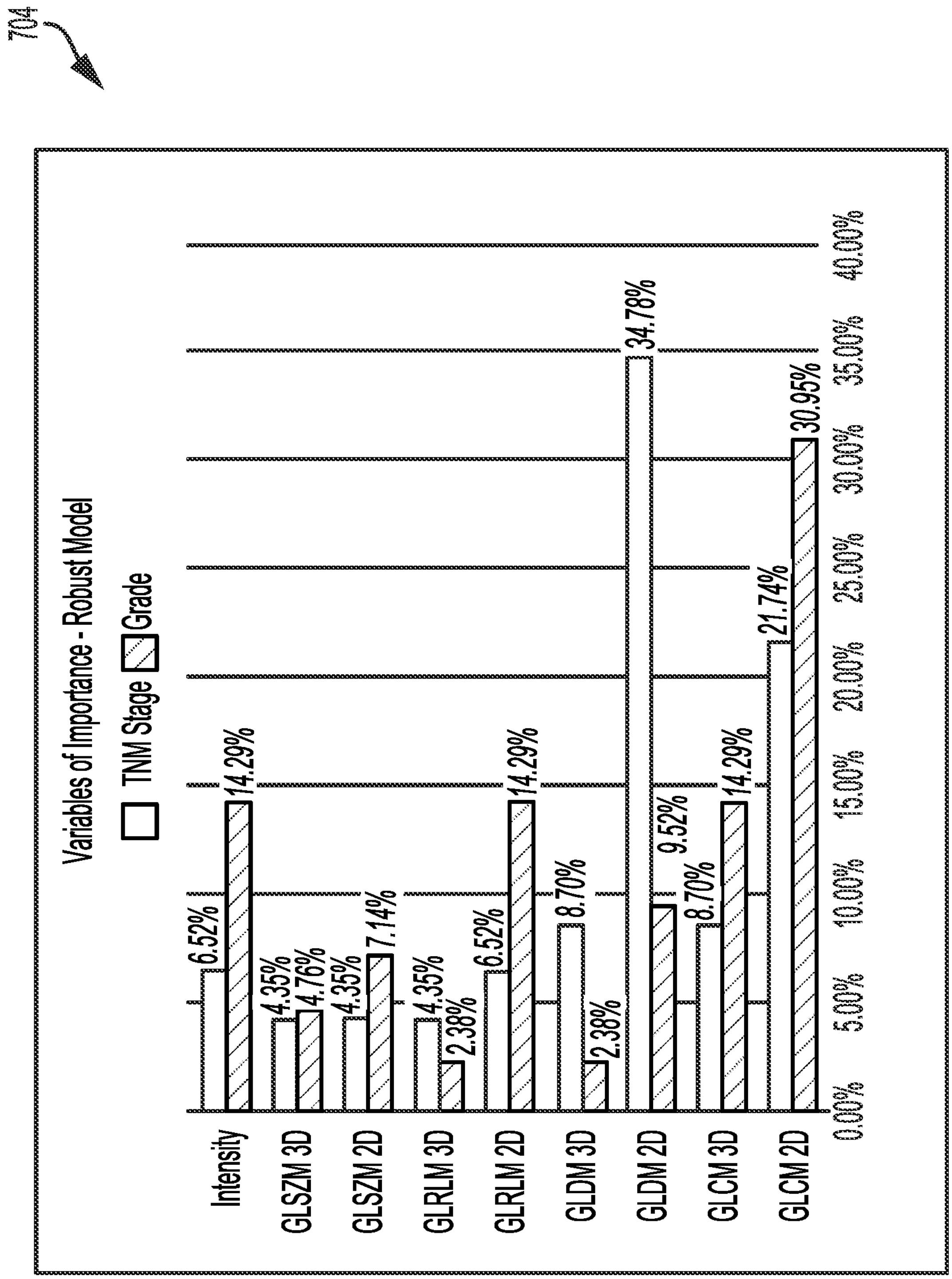
FIG. 7B is a chart illustrating a distribution of VOI across all machine learning classifiers for the robust model, in accordance with various embodiments.

Variables of importance. FIG. 7A is a chart 702 illustrating a distribution of VOI across all machine learning classifiers for the full model. FIG. 7B is a chart 704 illustrating a distribution of VOI across all machine learning classifiers for the robust model. Table 5 lists the top VOI for each model.

TABLE 5

Top Variables of Importance

| | Full Model | Robust Model |
|---|---|---|
| Grade | DCT 2D (30.23%)<br>LTE 3D (23.26%)<br>FFT 2D (9.30%) | GLCM 2D<br>*GLCM 3D<br>*Intensity<br>*GLRLM 3D |
| Stage | DCT 2D (29.27%)<br>LTE 2D (29.27%)<br>LTE 3D (12.20%) | GLDM 2D<br>GLCM 2D (21.74%)<br>*GLCM 3D (8.70%)<br>*GLDM 3D (8.70%) |

The proportion of metrics in a texture family which met variables of importance criteria is represented by the percentages in Table 5. An asterisk '*' denotes metrics found to demonstrate equal importance in the VOI ranking procedure.

Interobserver reliability assessment and sensitivity analysis. In the segmentation reliability assessment between three radiologists, 65% of radiomics features met ICC>0.80. Sensitivity analysis with all three machine learning classifiers showed that the prediction models using only the robust radiomics metrics performed comparably to the full model for both prediction tasks.

Discussion. This analysis investigates the utility of radiomics-based machine learning augmented prediction of tumor grade and TNM stage using multi-centric data for both training and external validation of the machine learning algorithm. To increase reproducibility, the analysis includes sensitivity analyses on the dependency of results based on the following factors: (1) manual segmentation by multiple users, (2) choice of machine learning classifiers to create the radiomics signatures, and (3) choice of radiomics panel (i.e., full model versus reduced model). The results highlight the consistency of the findings under various test conditions in the two classification tasks despite heterogeneity of the imaging data. This analysis is the first to demonstrate extensive external validation of an in-house radiomics pipeline on a diverse, multi-centric, common-source dataset. This represents an important step in establishing the generalizability of radiomics-based decision algorithms.

The results for distinguishing tumor grades were indicative of discriminative power. RF demonstrated the best performance on both the full and robust models with AUCs of 0.70 and 0.73, respectively. Adaboost and Elastic Net reported lower AUCs, but not overly different from those obtained by RF.

This method also employs 3D texture analysis, which is further representative of the tumor's spatial texture and therefore more reflective of subtle variations in intratumoral microenvironments.

Based on VOI analysis, the top texture families contributing to the performance of the full model in stratifying tumor grade were higher order statistical texture measures derived using spatial filtering methods (e.g., Discrete Cosine Transform (DCT) 2D, Laws Texture Energy (LTE) 3D, and Fast Fourier Transform (FFT) 2D) (see FIGS. 7A-B). There is a role for spatial filtering measures such as FFT-based metrics in determining ccRCC grade. For example, there is a significant difference in the FFT-based complexity index between different tumor grades in all four phases of CECT acquisition. A positive correlation is observed between tumor grade and complexity index. The FFT-based complexity index is significantly different between the juxtatumoral fat surrounding high-grade versus low-grade ccRCC.

Given the heterogeneity of the imaging data, the method herein is conducted with VOI analysis for grade stratification using the robust model. Top performing texture families contributing to the model's performance were second-order statistical texture measures derived using neighborhood-based analysis (e.g., GLCM 2D, GLCM 3D, and GLRLM 3D)-which consider the spatial distribution of gray levels in an image—and first-order statistical texture measures derived from Intensity assessment. Using ROC analysis, the Maximal Correlation Coefficient in GLCM analysis may have an AUC of 0.75 when differentiating between textural differences of juxtatumoral perinephric fat surrounding high-versus low-grade ccRCC. Multiphase CT from 65 ccRCC patients reveals that absolute enhancement is more heterogeneous for lower grade tumors. Observations support the assertion that CT-based textural differences exist between low and high ccRCC tumor grade and that these can be extracted using first- and second-order texture measures to create predictive models of tumor behavior.

In line with the grade stratification findings, RF was also the best performing decision classifier for TNM stage stratification with AUCs of 0.80 and 0.77 in the full model and robust model, respectively.

With this method, metrics with large differences between institutions and scanners would be expected to drop out as any unstable signals mostly negate each other. Additionally, while the nephrographic phase provided the best delineation of the tumors when compared to other phases, 16 subjects unfortunately did not have nephrographic scans available for analysis. In these cases, this effort opted to use the CT phase in which the tumor was most prominently visible to serve as a segmentation template to co-register the other phases. Developing an approach that is agnostic of a given phase (which may not be standardized across multiple centers) and rather based on tumor visibility is an option in radiomics analyses in order to maximize sample size.

Shape and Texture-Based Radiomics Signature on CT Effectively Discriminates Benign from Malignant Renal Masses Notably, and as indicated, in various embodiments, a radiomics framework quantitatively analyzes tumor shape and texture features in three dimensions. Such a framework is able to objectively and robustly distinguish between benign and malignant renal masses. In various instances, an evaluation is provided of the relative contributions of shape and texture metrics separately and together in the prediction model. Computer tomography (CT) images of 735 patients with 539 malignant and 196 benign masses were segmented in this analysis. Thirty-three shape and 760 texture metrics were calculated per tumor. Tumor classification models using shape, texture, and both metrics were built using random forest and AdaBoost with tenfold cross-validation. Sensitivity analyses on five sub-cohorts with respect to the acquisition phase were conducted. Additional sensitivity analyses after multiple imputation were also conducted. Model performance was assessed using AUC.

A random forest classifier showed shape metrics featuring within the top 10% performing metrics regardless of phase, attaining the highest variable importance in the corticomedullary phase. Convex hull perimeter ratio is a consistently high-performing shape feature. Shape metrics alone achieved an AUC ranging 0.64-0.68 across multiple classifiers, compared with 0.67-0.75 and 0.68-0.75 achieved by texture-only and combined models, respectively. Shape metrics alone attain high prediction performance and high variable importance in the combined model, while being independent of the acquisition phase (unlike texture). Shape analysis therefore should not be overlooked in its potential to distinguish benign from malignant tumors, and future radiomics platforms powered by machine learning should harness both shape and texture metrics.

Most renal tumors are incidentally diagnosed on routine imaging. Nevertheless, accurate preoperative characterization of renal masses carries a significant error rate, as discussed in earlier sections of this disclosure. Currently, ~20% of renal masses turn out to be benign following resection, with the majority being <4 cm in diameter, and identifying these patients beforehand could potentially spare them from unneeded surgery.

In routine clinical practice, a combination of qualitative and semi-quantitative evaluation is used to classify a renal mass as likely "benign" or "malignant." Visual assessments of tumor size, shape, texture, and enhancement are all important for determining the likelihood of cancer. In contrast to enhancement being a quantifiable parameter measured in Hounsfield units on CT, tumor shape has typically been a qualitative assessment, making visual analysis of tumor contour subjective and susceptible to inter- or intra-observer interpretation variability.

In radiomics, quantitative tumor features such as size, shape, and texture are extracted from routine images. While most radiomics studies are heavily weighted towards applying texture analysis to distinguish various renal mass subtypes, the literature on shape analysis is relatively sparse. Irregular morphology may be an independent predictor of higher grade clear cell RCC. There is a need for further systems and methods to distinguish benign from malignant renal masses by harnessing the wide array of shape and texture features. Though this has been introduced and discussed above, further explication herein below is useful.

In various embodiments, malignant masses tend to be more lobulated and non-spheroidal and show different textures than benign masses, as well as the fact that shape and texture metrics were robust to manual segmentation. Prior efforts leave the relative contributions of tumor shape versus texture to malignant behavior unclear.

In this disclosure, using a larger cohort compared with 150 patients from prior studies, various embodiments assess both classes of metrics to noninvasively differentiate benign from malignant renal masses. This disclosure analyzes the relative contributions of shape versus texture of a tumor on standard-of-care imaging to its malignant potential and the improvement in classification when combining the two and evaluates the necessity and contribution of shape metrics to the prediction model.

The patient population includes renal masses diagnosed on abdominal CT scans with pathologic diagnoses confirmed after resection at our institution. Patients were identified by retrospective query of a prospectively maintained surgical database of 1178 consecutive radical or partial nephrectomies between May 2007 and September 2018. Pathologic evaluation was performed by specialized genitourinary pathologists.

One hundred twelve patients were excluded due to the absence of evaluable preoperative imaging within a year before the nephrectomy. 49 patients were excluded with tumors arising outside the renal parenchyma, such as retroperitoneal liposarcoma, perirenal cyst, adrenal pseudocyst, and urothelial carcinoma. 74 cases were excluded that lacked contrast-enhanced CT images, since tumor margins are difficult to accurately segment on non-contrast images. Two hundred eight cases were unable to be processed, largely due to digital imaging and communications in medicine (DICOM) incompatibilities from outside institutions that precluded processing in the radiomics pipeline.

Figure 8:
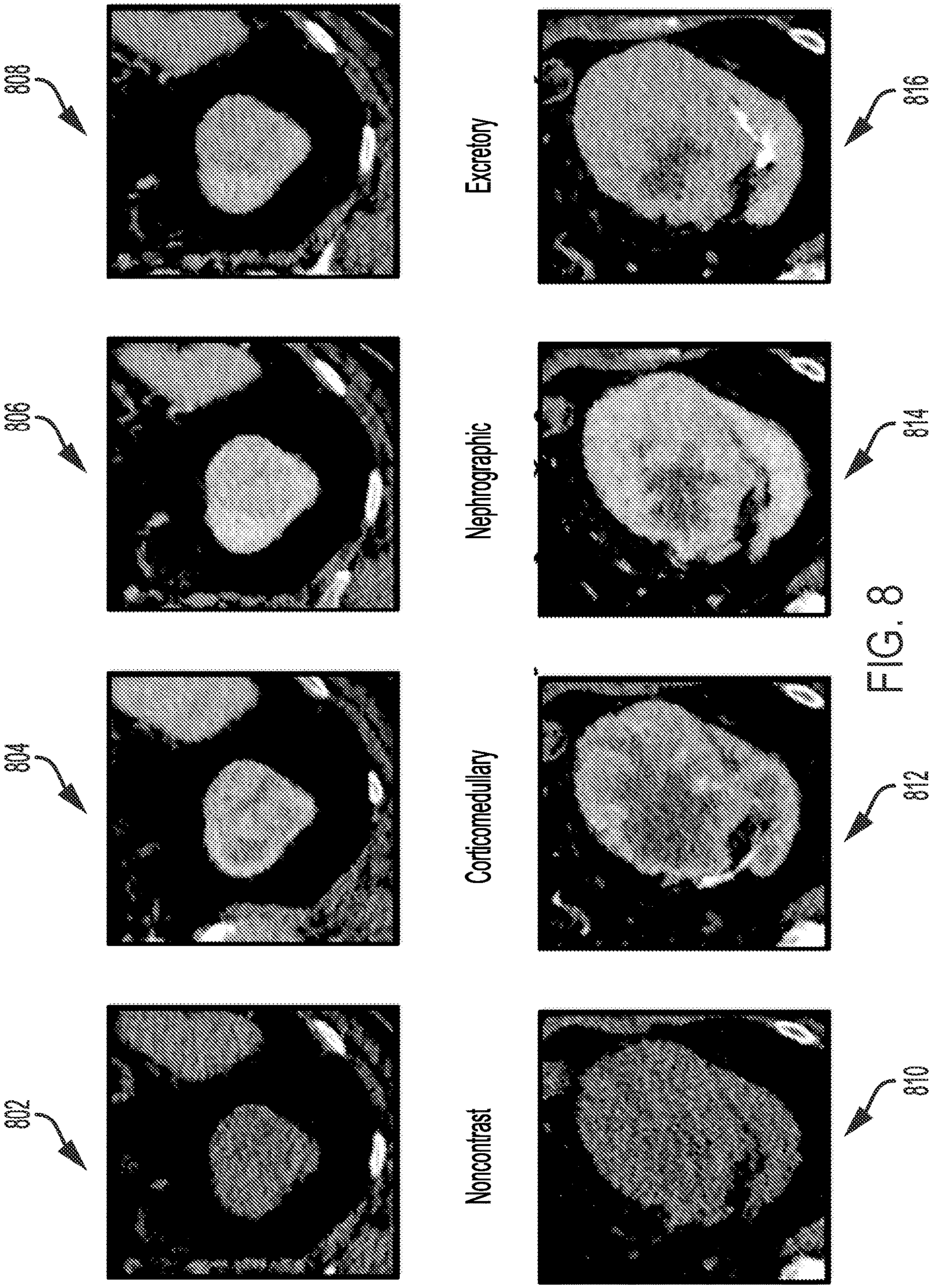
FIG. 8 shows a series of multiphase axial CT images that show a 77-year-old male with a 3.7-cm left renal mass that proved to be a chromophobe renal cell carcinoma and that show a 69-year-old male with an 8.0-cm left renal mass that proved to be an oncocytoma, in accordance with various embodiments.

The final cohort contained 539 malignant and 196 benign masses and includes texture analysis and more renal mass subtypes, especially benign ones, to assess the integrated radiomics platform's role in renal mass evaluation. Preoperative CTs were obtained in 308/735 patients (42%), where a 64-detector row helical CT scanner (Brilliance, Philips Healthcare) was used to acquire images during patient breath-holding with these parameters: 120 kVp, variable tube current, slice thickness of 0.5 mm with reconstruction interval of 2 mm. In total, 100-150 mL of nonionic intravenous contrast material (ISOVUE® 350; Bracco Imaging) dosed to weight was administered with a power injector at a rate of 4-5 mL/s. These images are illustrated in FIG. 8, which shows a series of multiphase axial CT images 802, 804, 806, 808 that show a 77-year-old male with a 3.7-cm left renal mass that proved to be a chromophobe renal cell carcinoma, stage pT3a. These images include non-contrast 802, corticomedullary (30 s) 804, nephrographic (90 s) 806, and excretory (5-7 min) 808 phase images of the abdomen. FIG. 8 also shows a series of multiphase axial CT images 810, 812, 814, and 816 that show a 69-year-old male with an 8.0-cm left renal mass that proved to be an oncocytoma. These images include non-contrast 810, corticomedullary (30 s) 812, nephrographic (90 s) 814, and excretory (5-7 min) 816 phase images of the abdomen.

The remaining patients had preoperative imaging performed at outside institutions prior to referral to our institution for surgical resection, but their CT examinations were uploaded onto our picture archiving and communication system (PACS) and thus available to be segmented and included in the cohort for processing in our radiomics pipeline.

Tumor Segmentation.

Using Synapse 3D software (Fujifilm), two senior radiologists-in-training manually segmented renal tumors as three-dimensional regions of interest being blinded to pathologic diagnoses. Segmentation times varied from 20 to 40 min per case. Segmentations were then verified for accuracy by two radiologists with 5 and 20 years of experience in abdominal imaging. In general, the nephrographic phase provided the best delineation of the tumor and hence was used as the reference target for subsequent coregistration of other phases. If the nephrographic phase was not available for that case, the corticomedullary or excretory phase became the reference target instead. Images were coregistered by using the normalized mutual information cost function implemented in the Statistical Parametric Mapping software package (Wellcome Centre for Human Neuroimaging). Tessellated 3-D models of the tumor were created from segmented voxels using custom MATLAB (MathWorks) code.

Tumor Shape and Texture Analyses.

Shape analysis utilizes metrics to characterize the morphology, whereas texture analysis studies the variation of pixel intensity and their interrelationships. Shape analysis was performed for the whole tumor volume in the axial, coronal, and sagittal projections. Two-dimensional texture analysis was conducted in the orientation providing the largest tumor area in each phase in the axial, coronal, or sagittal projection. Three-dimensional texture analysis was conducted on the whole tumor volume.

In the case of shape metrics, some of these metrics are shown in Table 6 below. Shape analysis is performed using 33 shape metrics. Each shape feature focuses on certain characteristics of tumor morphology and factors into a quantitative calculation.

TABLE 6

| Lower Range | Characteristic | Upper Range |
|---|---|---|
| 0 (less compact) | Compactness, Sphericity | 1 (more compact) |
| 0 (more irregular) | RD Mean | 1 (circular) |
| 1 (more irregular) | RD Standard Deviation | 0 (circular) |
| Infinity (more lobulated) | RD Area Ratio | 0 (circular) |
| Infinity (more meandering contour) | ZC | 0 (less meandering contour) |
| Infinity (more irregular) | Entropy | 0 (more compact) |
| 0 (more oblong) | Feret Ratio | 1 (spherical) |
| 0 (more lobulated) | CHA, CHP | 1 (no lobulations) |
| 0 (less ellipsoid) | Elliptic Compactness | 1 (more ellipsoid) |

Texture analysis is also performable using 760 texture metrics. Each texture metric involves a study of the variation of pixel image intensity. Different classes of texture metrics entail gray-level histogram analysis, gray-level co-occurrence matrix (GLCM) analysis, gray-level difference matrix (GLDM) analysis, and frequency analysis based on fast Fourier transform (FFT). For instance, gray-level histogram analysis may include kurtosis, mean, quartile range, standard deviation, skewness, and median. GLCM/GLDM analysis may include correlation, dissimilarity, entropy, homogeneity, uniformity, and variance. FFT analysis may include entropy of FFT magnitude, entropy of FFT phase, and complexity index.

Reliability Assessment.

A reliability analysis was conducted with 3 radiologists. Each radiologist segmented the margins independently for 15 subjects. Intraclass correlation (ICC) 2-way-mixed with absolute agreement was used to evaluate reliability.

Machine Learning Prediction Rule Development and Statistical Analysis.

Random forest was used as the primary method for classifier development. This system and method used average square error plots to select optimal numbers of decision trees and variables to try for each tree-building and leaf size. For bootstrapping at each tree, 60% of the original observations were used. Tenfold cross-validation was used to obtain robust classification performance. AUC was used to assess robust discrimination power based on predicted probability from each fold of testing data. The out-of-bag Gini index was used to rank the variable of importance. The gain in discriminatory power was assessed by comparing the full model (combined texture and shape classifier) vs. reduced model (e.g., texture only). Z test was used to compare AUCs.

For sensitivity analysis, 5 sub-cohorts of cases with respect to the acquisition phase were created. Sub-cohort I included cases that contain all four individual phases (non-contrast, corticomedullary, nephrographic, and excretory). Sub-cohorts II to IV include cases that contain a specific individual phase. Random forest classifiers were built and validated using these 5 sub-cohorts respectively. The above procedures were repeated using AdaBoost as well.

Many machine learning methods eliminate missing data such as data with missing phases within multiphase CT data. To apply those methods to data with a high missing rate, the system and method imputed missing data using the Markov Chain Monte Carlo (MCMC). This approach also helped compare the MCMC methodology based on built-in procedures of random forest and AdaBoost in dealing with data missingness using surrogate data. The average score across 10 imputed datasets was used for the final imputed data. Using the completed data after imputation, more classifiers were developed and validated: ElasticNet, random forest, AdaBoost, MARS, and NeuroNet. Model performance was validated through ⅓ independent testing data. To further test model robustness, the model was rebuilt using data from one institute and validated through other institutes. SAS 9.4 was used for all data analyses.

Five hundred thirty-nine of 735 (73%) patients with malignant renal tumors and 196/735 (27%) patients with benign renal tumors were included in the final patient cohort. Among clear cell RCCs, 135/401 (34%) were of high-grade (ISUP grades 3-4) and 77/401 (19%) were stage T3 or higher. Among stage T1 RCCs, 290/397 (73%) were T1a and 107/397 (27%) were T1b. In total, 495/735 (67%) patients were male. The mean age was 60.8 (range 17-93).

In the segmentation reliability assessment between 3 radiologists, 65% of features met ICC>0.8. Thus, a sensitivity analysis was conducted with random forest using these robust features only. Using robust features only reached similar performance as using all features.

Of the various metrics, the convex hull perimeter ratio (CHP) ranked consistently as a high-performing shape feature across all four phases, followed by elliptic compactness (EC). Of all four phases, shape metrics featured most prominently in the corticomedullary phase (sub-cohort III), with CHP and EC both featuring as highly ranked within the top 10%. This has been repeated 10 and 6 times respectively during the tenfold cross-validation. In 4-phase sub-cohort I, CHP ranked among the top 67 metrics, appearing 3 times during the tenfold cross-validation. CHP also appeared 9 times in the non-contrast phase, 3 times in the nephrographic phase, and 7 times in the excretory phase during the tenfold cross-validation.

Comparison Between Shape-Only, Texture-Only, and Combined Models.

Table 7 is a tabulation of the segregation of various radiomics models obtained using shape only, texture only, and combined shape and texture metrics. In Table 7, an asterisk '*' means significant gain (p<=0.05).

TABLE 7

| Model | Sub-cohort I: all 4 phase | Sub-cohort II: non-contrast phase | Sub-cohort III: corticomedullary phase | Sub-cohort IV: nephrographic phase | Sub-cohort V: excretory phase |
|---|---|---|---|---|---|
| 1 = shape only | 0.64 | 0.65* | 0.68* | 0.64 | 0.66 |
| 2 = texture only | 0.75* | 0.70* | 0.70* | 0.67 | 0.69 |
| 3 - combined | 0.75 | 0.71 | 0.73 | 0.68 | 0.70 |

Figure 9:
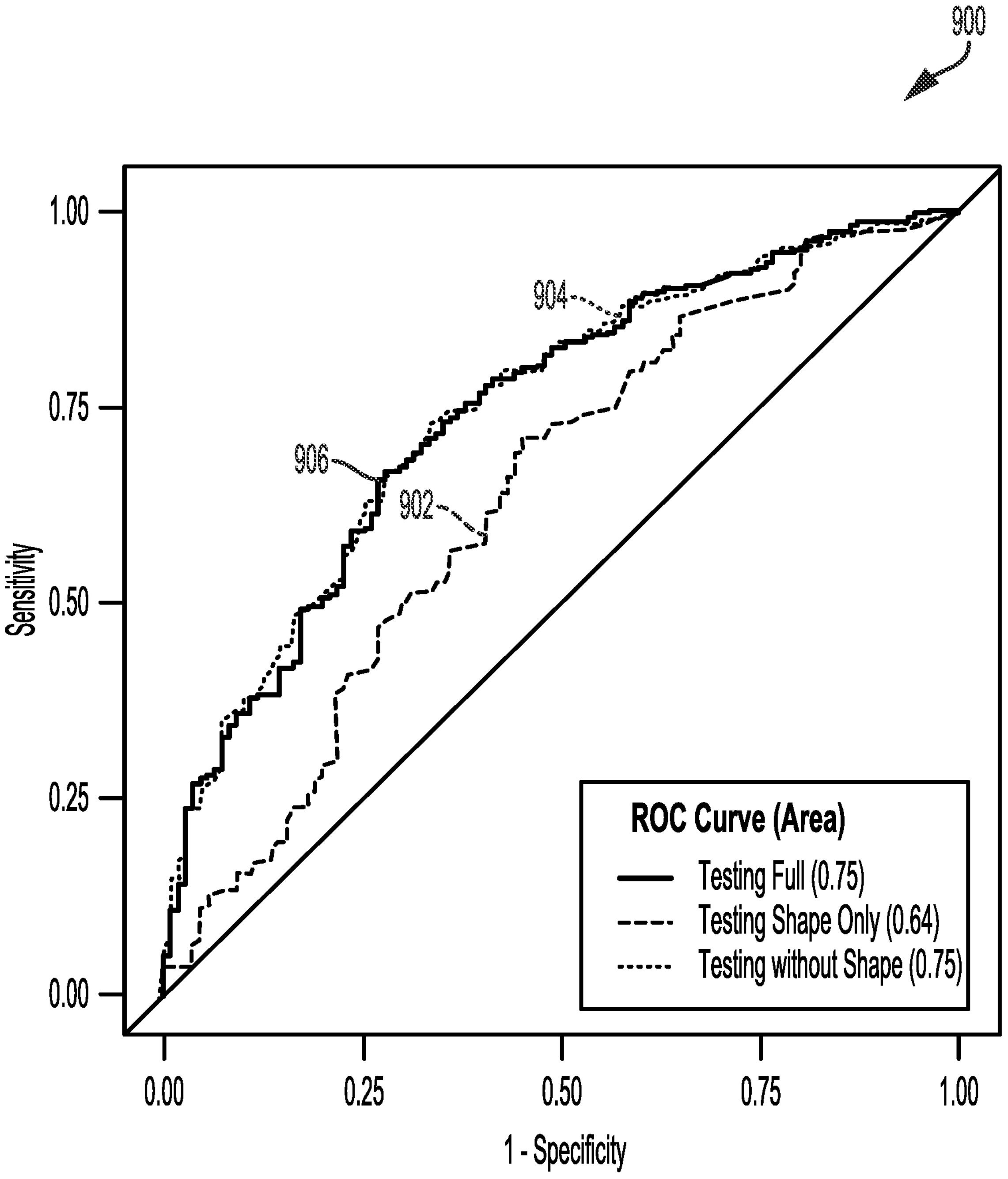
FIGS. 9-10 shows various graph illustrating receiver operating characteristic (ROC) curves for different radiomics models in the discrimination of benign and malignant renal masses using imaging data, in accordance with various embodiments.
Figure 10:
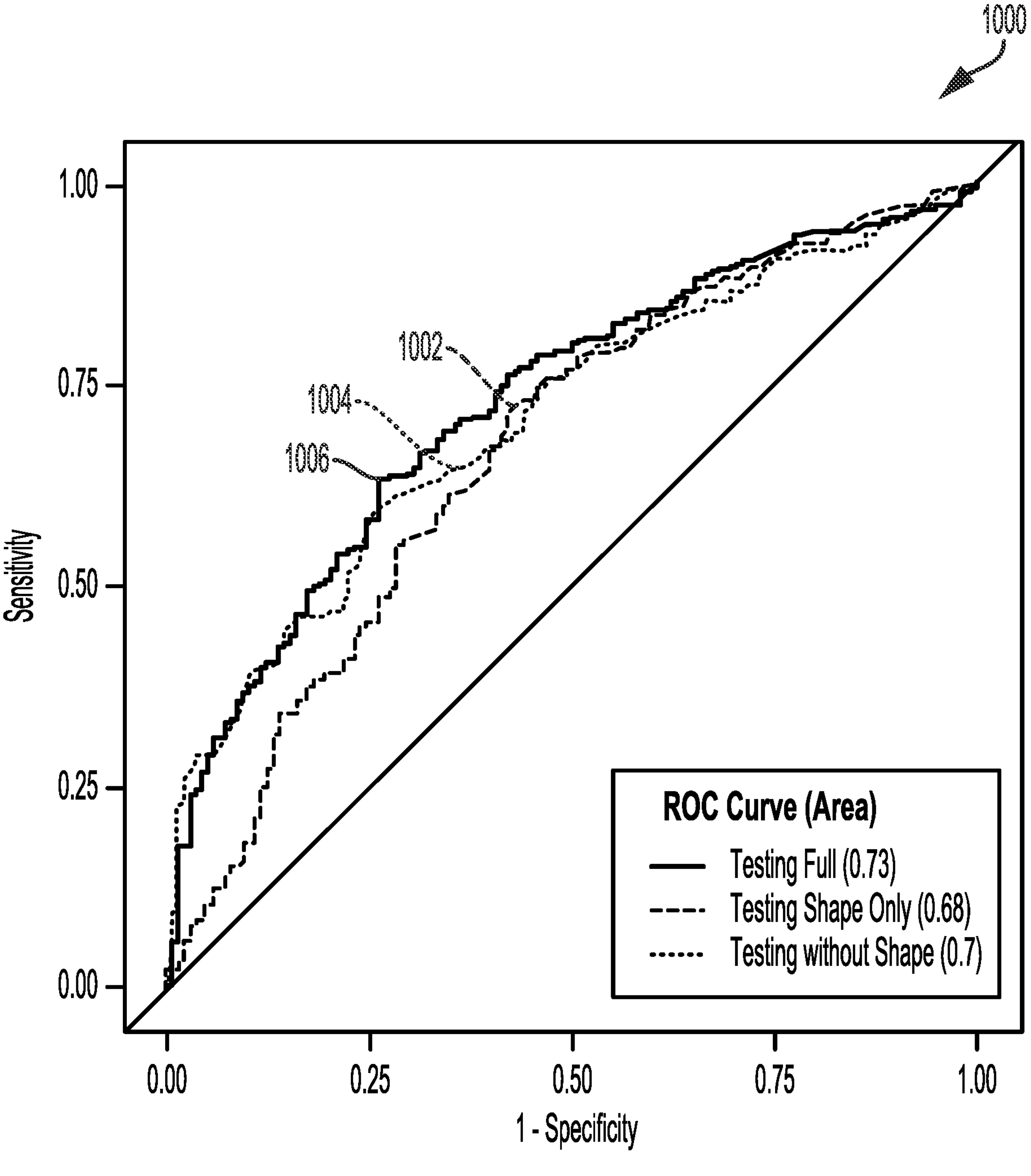

In sub-cohort I entailing 4-phase studies (n=453), an AUC of 0.64 in the independent testing subset was achieved by 33 shape metrics alone, whereas an AUC of 0.75 was achieved using 760 texture metrics (FIG. 9). Sensitivity analyses conducted in different individual phases with complete data also demonstrated similar results (FIG. 10), although the gaps between the AUCs for the isolated models were narrower. Shape-only models also attained comparable performance in the nephrographic and excretory phase sub-cohorts IV and V (AUCs 0.64 and 0.66 respectively, in comparison with 0.67 and 0.69 for texture-only models). Turning more specifically to FIG. 9, graph 900 illustrates receiver operating characteristic (ROC) curves for the shape-only 902, texture-only 904, and combined 906 radiomics models in the discrimination of benign and malignant renal masses using imaging data with all four phases available (sub-cohort I). AUC values are shown in the lower right corner. Turning more specifically to FIG. 10, receiver operating characteristic (ROC) curves are illustrated for the shape-only 1002, texture-only 1004, and combined 1006 radiomics models in the discrimination of benign and malignant renal masses using imaging data with a corticomedullary phase available (sub-cohort III). AUC values are shown in the lower right corner.

The texture-only model's performance slightly increased from 0.67-0.70 in the individual phase sub-cohorts II-V to 0.75 when all 4 phases are analyzed in sub-cohort I, whereas the shape-only model's performance was consistently in a similar range (0.64-0.68) regardless of whether all 4 phases or only individual phases were considered. This result is not surprising, given that the prediction rule from texture analysis is expected to improve in performance as additional data from multiple phases are included in the learning phase, whereas shape analysis is independent of the acquisition phase and its performance thus would not vary with phase(s).

Table 8 shows the gain in AUC by adding texture analysis to the shape-only model and vice versa. For sub-cohort I with all 4 phases, adding shape analysis to the combined model did not improve discrimination over the texture-only model (0.75 vs. 0.75, p=0.77). However, within the corticomedullary phase sub-cohort III, even though texture metrics alone attained an AUC of 0.70, adding shape analysis to this sub-cohort significantly increased the AUC to 0.73 in the combined model (p<0.01). Values are mean gain in AUC with 95% CI and p value in parentheses. The symbol '+' denotes significant gain (p≤0.05).

TABLE 8

| Comparison | Sub-cohort I: all 4 phases AUC | Sub-cohort II: non-contrast phase AUC | Sub-cohort III: corticomedullary phase AUC | Sub-cohort IV: nephrographic phase AUC | Sub-cohort V: excretory phase AUC |
|---|---|---|---|---|---|
| Texture contribution: gain of model 3 over model 1 | 0.11 (0.05 to 0.17, p < 0.01)† | 0.06 (0.02 to 0.11, p = 0.01)† | 0.05 (0 to 0.10, p = 0.04)† | 0.04 (−0.01 to 0.10, p = 0.11) | 0.04 (−0.01 to 0.10, p = 0.12) |

TABLE 8-continued

| Comparison | Sub-cohort I: all 4 phases AUC | Sub-cohort II: non-contrast phase AUC | Sub-cohort III: corticomedullary phase AUC | Sub-cohort IV: nephrographic phase AUC | Sub-cohort V: excretory phase AUC |
|---|---|---|---|---|---|
| Shape contribution: gain of model 3 over model 2 | 0.00 (−0.01 to 0.01, p = 0.77) | 0.01 (0 to 0.02, p = 0.05)† | 0.03 (0.01 to 0.04, p < 0.01)† | 0.01 (0 to 0.02, p = 0.09) | 0.01 (0 to 0.02, p = 0.06) |

There was comparable performance between AdaBoost and random forest, as they work well with missing data. Performance did not deviate significantly using random forest with the 4-phase complete data.

Using a previously validated quantitative panel of metrics, different radiomics models were built based on 33 shape and 760 texture features from random forest classifiers. Results show that for the task of distinguishing benign from malignant renal masses, shape metrics alone attain a reasonably high prediction performance and hold high variable importance in the combined radiomics model, while being independent of the acquisition phase (unlike texture).

Of all shape metrics, the convex hull perimeter ratio (CHP) was a consistently high-performing one regardless of phase, along with elliptic compactness (EC). This is concordant with results identifying these two features as statistically significant between benign and malignant renal masses. The CHP metric may be analogous to the fractional concavity feature described in the image biomarker standardization initiative, which is a reliable shape feature least affected by slice thickness or volume changes. As for EC (also termed anfractuosity or elliptic-normalized circumference), it appears that EC most resembles the volume/area density—minimum volume enclosing ellipsoid feature in the image biomarker standardization initiative.

Shape metrics may be more robust than texture metrics with respect to different imaging parameters and respiratory motion patterns in the setting of some tumors such as lung tumors. Given that texture features are less reliable than shape, and that tumor shape itself is independent of phase acquisition and hence more stable, in some embodiments, the inclusion of shape analysis alongside texture may have benefits. When using combined features including both texture and shape, several shape features attained high-rank positions. The correlation between texture and shape especially with high-dimensional data results, in various embodiments, in competitive performance between the combined and texture-only models. However, when encountering missing or poor-quality data in real life, the shape can at least serve as a surrogate marker when texture feature is missing, of poor quality, or unstable between different scanners.

When presented with the challenge of high data dimensionality, machine learning such as a random forest is a prime method for dimensional reduction. Using other dimension reduction methods prior to random forest could be problematic due to data loss (e.g., feature filtered prior to learning) and poor stability (e.g., a principal component derived from learning sample may not fit well in the testing sample). From a radiomics analysis standpoint, the model provided herein will assess all features. In addition, given that one of radiomics' strengths is the numerous features that are computable from radiologic images, discarding features using statistical criteria without ascertaining their roles in the clinical question poses a risk for losing valuable information.

This discussion demonstrates that shape metrics alone, especially convex hull perimeter ratio and elliptic compactness, can attain a similar discriminatory power as texture metrics, signifying that shape analysis should not be overlooked in a radiomics platform powered by machine learning. A framework as such may utilize both shape and texture together rather than in isolation from each other.

Figure 11:
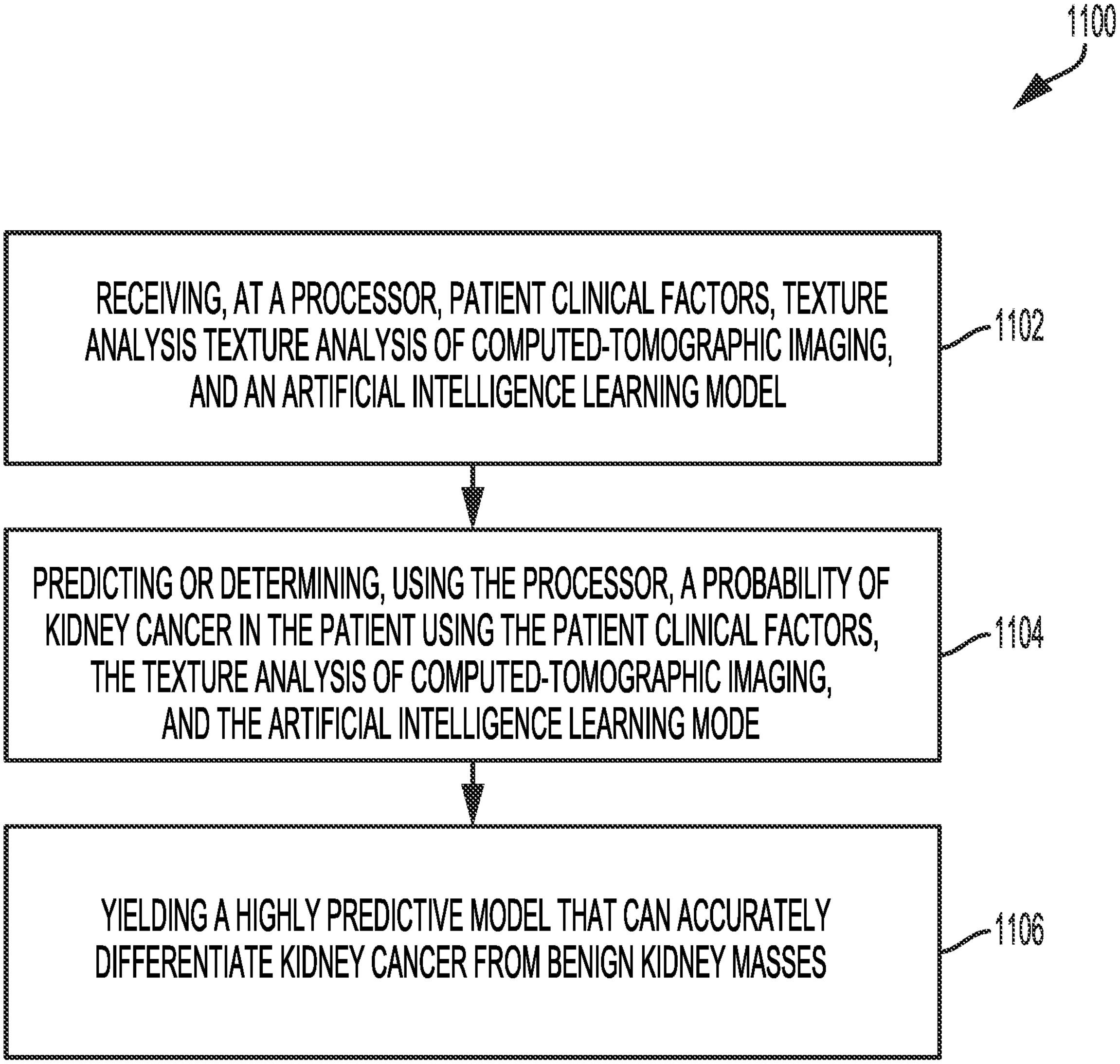
FIG. 11 illustrates a method of non-invasive, non-surgical, digital biopsy for accurately predicting benign kidney lesions from cancers in a patient, in accordance with various embodiments.

Turning now to FIG. 11, but with ongoing reference to the above discussion and FIGS. 1-10, a method 1100 is provided of non-invasive, non-surgical, digital biopsy for accurately predicting benign kidney lesions from cancers in a patient. The method may include multiple aspects, which have been discussed at length herein above. For instance, the method may include receiving, at a processor, patient clinical factors, texture analysis texture analysis of computer-tomographic imaging, and an artificial intelligence learning model (block 1102). The method may include predicting or determining, using the processor, a probability of kidney cancer in the patient using the patient clinical factors, the texture analysis of computer-tomographic imaging, and the artificial intelligence learning model (block 1104). Discussions at length above capture various embodiments and variations for the predicting or determining. In various embodiments, the using of the patient clinical factors, the texture analysis of computer-tomographic imaging, and the artificial intelligence learning model yields a highly predictive model that can accurately differentiate kidney cancer from benign kidney masses (block 1106). Stated differently, a predictive model may be generated responsive to the predicting or determining of a probability.

In various embodiments, the patient clinical factors include at least one of age, gender, race, co-morbid conditions, local symptoms at diagnosis, smoking status, family history, renal function, renal mass size or tumor-specific variables. Moreover, within the performing of the texture analysis of computer-tomographic imaging, the processor may perform two-dimensional shape and texture analysis on a largest tumor diameter within each imaging plane or performing three-dimensional shape and texture analysis on an entire tumor volume. The texture analysis of computer-tomographic imaging may include molecular imaging using radionuclide tagged probes detected with positron emitted tomography or single photon emission computed tomography.

In various embodiments, the artificial intelligence learning model includes image analysis to increase the accuracy of the probability of kidney cancer in the patient. The artificial intelligence learning model may include radiomic-based predictive modeling. The artificial intelligence learning model includes a machine-learning predictive model that incorporates radiomic analysis. Other machine learning models are contemplated.

Figure 12:
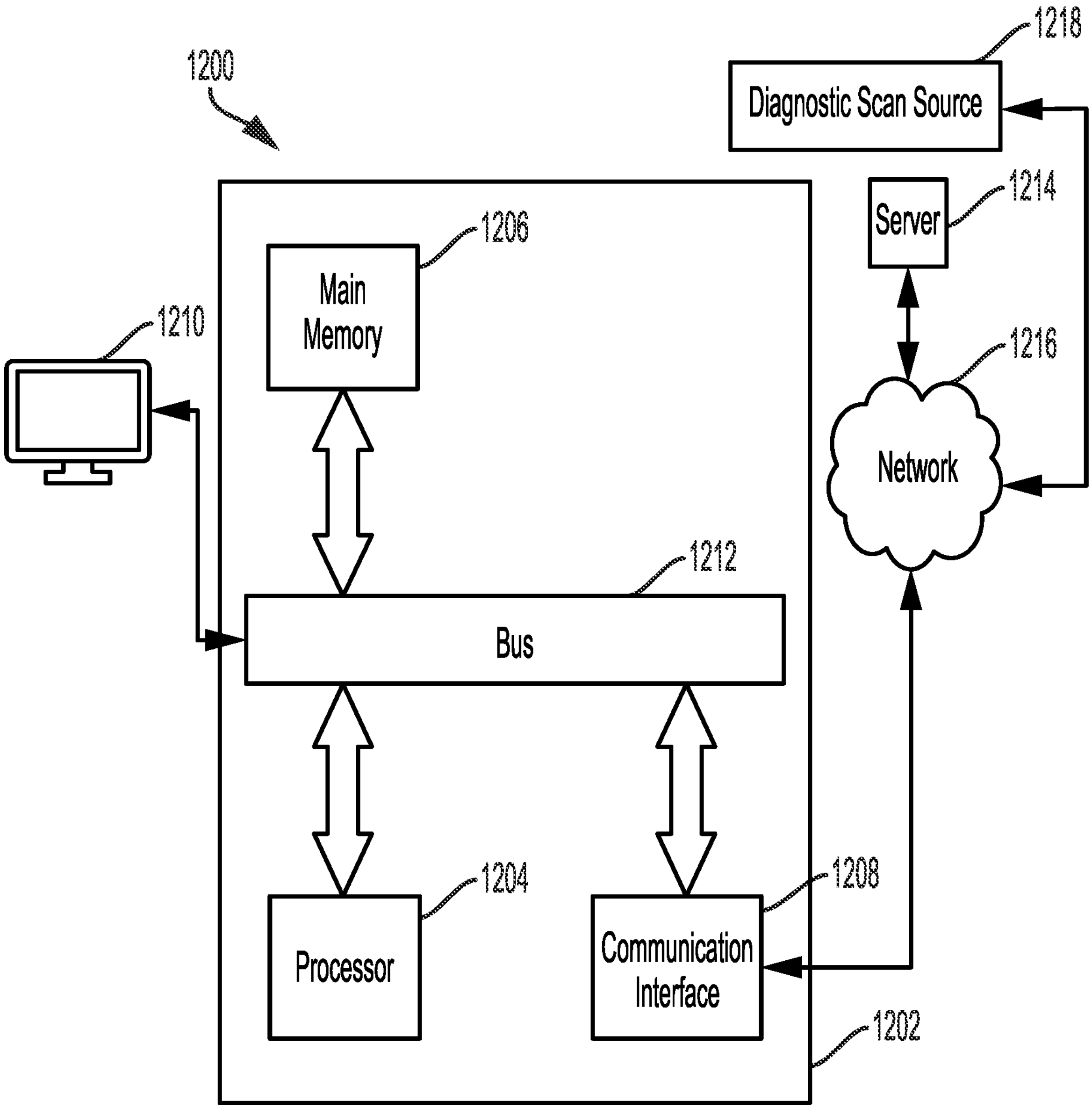
FIG. 12 illustrates a non-invasive, non-surgical, digital biopsy system, in accordance with various embodiments.

Turning now to FIG. 12, an example embodiment of a non-invasive, non-surgical, digital biopsy system may include a computing system 1200. The computing system 1200 may include a computing apparatus 1202. The computing apparatus 1202 may include one or more processors 1204, a memory 1206 and/or a bus 1212 and/or other mechanisms for communicating between the one or more processors 1204. The one or more processors 1204 may be implemented as a single processor or as multiple processors. The one or more processors 1204 may execute instructions stored in the memory 1206 to implement the applications and/or detection of the computing system 1200.

The one or more processors 1204 may be coupled to the memory 1206. The memory 1206 may include one or more of a Random Access Memory (RAM) or other volatile or non-volatile memory. The memory 1206 may be a non-transitory memory or a data storage device, such as a hard disk drive, a solid-state disk drive, a hybrid disk drive, or other appropriate data storage, and may further store machine-readable instructions, which may be loaded and executed by the one or more processors 1204.

The memory 1206 may include one or more of random access memory ("RAM"), static memory, cache, flash memory and any other suitable type of storage device or computer readable storage medium, which is used for storing instructions to be executed by the one or more processors 1204. The storage device or the computer readable storage medium may be a read only memory ("ROM"), flash memory, and/or memory card, that may be coupled to a bus 1212 or other communication mechanism. The storage device may be a mass storage device, such as a magnetic disk, optical disk, and/or flash disk that may be directly or indirectly, temporarily or semi-permanently coupled to the bus 1212 or other communication mechanism and be electrically coupled to some or all of the other components within the computing system 1200 including the memory 1206, the user interface 1210 and/or the communication interface 1208 via the bus 1212.

The term "computer-readable medium" is used to define any medium that can store and provide instructions and other data to a processor, particularly where the instructions are to be executed by a processor and/or other peripheral of the processing system. Such medium can include non-volatile storage, volatile storage and transmission media. Non-volatile storage may be embodied on media such as optical or magnetic disks. Storage may be provided locally and in physical proximity to a processor or remotely, typically by use of network connection. Non-volatile storage may be removable from computing system, as in storage or memory cards or sticks that can be easily connected or disconnected from a computer using a standard interface.

The system 1200 may include a user interface 1210. The user interface 1210 may include an input/output device. The input/output device may receive user input, such as a user interface element, hand-held controller that provides tactile/proprioceptive feedback, a button, a dial, a microphone, a keyboard, or a touch screen, and/or provides output, such as a display, a speaker, an audio and/or visual indicator, or a refreshable braille display. The display may be a computer display, a tablet display, a mobile phone display, an augmented reality display or a virtual reality headset. The display may output or provide a virtual environment that mimics actions of the patient and/or provide information regarding the neural activity of the patient or other information.

The user interface 1210 may include an input/output device that receives user input, such as a user interface element, a button, a dial, a microphone, a keyboard, or a touch screen, and/or provides output, such as a display, a speaker, headphones, an audio and/or visual indicator, a device that provides tactile/proprioceptive feedback or a refreshable braille display. The speaker may be used to output audio. The user interface 1210 may receive user input that may include configuration settings for one or more user preferences, such as a selection, for example.

The system 1200 may have a network 1216 that connects to a server 1214 and a diagnostic scan source 1218. The network 1216 may be a local area network (LAN), a wide area network (WAN), a cellular network, the Internet, or combination thereof, that connects, couples and/or otherwise communicates between the various components of the system 1200 with the server 1214. The server 1214 may be a remote computing device or system that includes a memory, a processor and/or a network access device coupled together via a bus. The server 1214 may be a computer in a network that is used to provide services, such as accessing files or sharing peripherals, to other computers in the network.

The system 1200 may include a communication interface 1208, such as a network access device. The communication interface 1208 may include a communication port or channel, such as one or more of a Dedicated Short-Range Communication (DSRC) unit, a Wi-Fi unit, a Bluetooth® unit, a radio frequency identification (RFID) tag or reader, or a cellular network unit for accessing a cellular network (such as 3G, 4G, or 5G). The communication interface may transmit data to and receive data among the different components.

The server 1214 may include a database. A database is any collection of pieces of information that is organized for search and retrieval, such as by a computer, and the database may be organized in tables, schemas, queries, reports, or any other data structures. A database may use any number of database management systems. The information may include real-time information, periodically updated information, or user-inputted information. For instance, the server may store probabilities or models generated by the methods herein.

The diagnostic scan source 1218 may include a database with images corresponding to diagnostic scans. In further instances, the diagnostic scan source 1218 may include a diagnostic scanner, such as a CT scanner or other scanner as desired. In various instances, the system 1200 controls the diagnostic scan source 1218 or provides instructions to the diagnostic scan source 1218 regarding images, or characteristics of images desired for retrieval for processing.

Thus, in various instances, the system 1200 has a diagnostic scan source 1218 comprising a computer-tomographic image scanner configured to generate a plurality of computer-tomographic images corresponding to at least one kidney of a patient, a server 1214 having a memory storing a plurality of patient clinical factors, and a processor 1204 connected to the diagnostic scan source 1218 and the server 1214 and configured to receive at the processor 1204 the patient clinical factors and the plurality of computer-tomographic images. The processor 1204 is configured to predicting or determining a probability of kidney cancer in the at least one kidney of the patient using the patient clinical factors, a texture analysis of the plurality of computer-tomographic images, and an artificial intelligence learning model.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

In various embodiments, software may be stored in a computer program product and loaded into a computer system using a removable storage drive, hard disk drive, or communications interface. The control logic (software), when executed by the processor, causes the processor to perform the functions of various embodiments as described herein. In various embodiments, hardware components may take the form of application specific integrated circuits (ASICs). Implementation of the hardware so as to perform the functions described herein will be apparent to persons skilled in the relevant art(s).

As will be appreciated by one of ordinary skill in the art, the system may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an Internet-based embodiment, an entirely hardware embodiment, or an embodiment combining aspects of the Internet, software, and hardware. Furthermore, the system may take the form of a computer program product on a computer-readable storage medium having computer-readable program code means embodied in the storage medium. Any suitable computer-readable storage medium may be utilized, including hard disks, CD-ROM, BLU-RAY DISC®, optical storage devices, magnetic storage devices, and/or the like.

What is claimed is:

1. A computer-implemented method for classification of a renal mass in a patient, the method comprising:

receiving, at a processor, a plurality of contrast-enhanced computed tomography image sets of the renal mass acquired in multiple CT phases, including at least a nephrographic phase image set and at least one additional phase image set;

generating a three-dimensional region of interest corresponding to the renal mass by segmenting the renal mass in the nephrographic phase image set;

co-registering the at least one additional phase image set to the nephrographic phase image set using a normalized mutual-information cost function to produce co-registered phase image sets;

extracting, from voxel data within the region of interest in the co-registered phase image sets, a radiomics feature vector that includes shape features computed on an entire tumor volume and texture features derived from at least one of: gray-level histogram analysis, gray-level co-occurrence matrix analysis, gray-level difference/dependence matrix analysis, or frequency analysis based on a fast Fourier transform;

applying to the radiomics feature vector a trained machine-learning classifier comprising a random forest classifier that (i) ranks variables of importance using an out-of-bag Gini index and (ii) was validated using tenfold cross-validation; and outputting, by the processor, a probability that the renal mass is malignant and a classification of the renal mass as benign or malignant based on the probability;

wherein the trained machine-learning classifier is trained using a reduced radiomics panel that comprises radiomics features predetermined to be robust across multiple CT scanners and imaging protocols based on an intraclass correlation coefficient criterion.

2. The computer-implemented method of claim 1, wherein the trained machine-learning classifier is further trained on at least one of age, gender, race, co-morbid conditions, local symptoms at diagnosis, smoking status, family history, renal function, renal mass size or tumor-specific variables.

3. The computer-implemented method of claim 1, wherein the texture analysis of computer-tomographic imaging includes performing two-dimensional shape and texture analysis on a largest tumor diameter within each imaging plane or performing three-dimensional shape and texture analysis on an entire tumor volume.

4. The computer-implemented method of claim 1, wherein the texture analysis of computer-tomographic imaging includes molecular imaging using radionuclide tagged probes detected with positron emitted tomography or single photon emission computed tomography.

5. The computer-implemented method of claim 1, wherein the trained machine-learning classifier is further trained using radiomic-based predictive modeling.

6. The computer-implemented method of claim 1, wherein the trained machine-learning classifier is further trained for radiomic analysis.

7. A non-transitory computer-readable medium comprising computer readable instructions, which when executed by a processor, cause the processor to perform operations for conducting a non-invasive, non-surgical, digital biopsy method for accurately predicting benign kidney lesions from cancers in a patient, the operations comprising:

receiving, at the processor, a plurality of contrast-enhanced computed tomography image sets of a renal mass acquired in multiple CT phases, including at least a nephrographic phase image set and at least one additional phase image set;

generating a three-dimensional region of interest corresponding to the renal mass by segmenting the renal mass in the nephrographic phase image set;

co-registering the at least one additional phase image set to the nephrographic phase image set using a normalized mutual-information cost function to produce co-registered phase image sets;

extracting, from voxel data within the region of interest in the co-registered phase image sets, a radiomics feature vector that includes shape features computed on an entire tumor volume and texture features derived from at least one of: gray-level histogram analysis, gray-level co-occurrence matrix analysis, gray-level difference/dependence matrix analysis, or frequency analysis based on a fast Fourier transform;

applying to the radiomics feature vector a trained machine-learning classifier comprising a random forest classifier that (i) ranks variables of importance using an out-of-bag Gini index and (ii) was validated using tenfold cross-validation; and outputting, by the processor, a probability that the renal mass is malignant and a classification of the renal mass as benign or malignant based on the probability;

wherein the trained machine-learning classifier is trained using a reduced radiomics panel that comprises radiomics features predetermined to be robust across multiple CT scanners and imaging protocols based on an intraclass correlation coefficient criterion.

8. The non-transitory computer-readable medium of claim 7, wherein the trained machine-learning classifier is further trained on at least one of age, gender, race, co-morbid conditions, local symptoms at diagnosis, smoking status, family history, renal function, renal mass size or tumor-specific variables.

9. The non-transitory computer-readable medium of claim 7, wherein the texture analysis of computer-tomographic imaging includes performing two-dimensional shape and texture analysis on a largest tumor diameter within each imaging plane or performing three-dimensional shape and texture analysis on an entire tumor volume.

10. The non-transitory computer-readable medium of claim 7, wherein the texture analysis of computer-tomographic imaging includes molecular imaging using radionuclide tagged probes detected with positron emitted tomography or single photon emission computed tomography.

11. The non-transitory computer-readable medium of claim 7, wherein the trained machine-learning classifier is further trained using radiomic-based predictive modeling.

12. The non-transitory computer-readable medium of claim 7, wherein the trained machine-learning classifier is further trained for radiomic analysis.

13. A system for non-invasive, non-surgical, digital biopsy for accurately predicting benign kidney lesions from cancers in a patient, the system comprising:

a diagnostic scan source comprising a computer-tomographic image scanner configured to generate a plurality of computer-tomographic images corresponding to at least one kidney of a patient;

a server having a memory storing a plurality of patient clinical factors; and a processor connected to the diagnostic scan source and the server and configured to: receive at the processor a plurality of contrast-enhanced computed tomography image sets of a renal mass acquired in multiple CT phases, including at least a nephrographic phase image set and at least one additional phase image set;

generate a three-dimensional region of interest corresponding to the renal mass by segmenting the renal mass in the nephrographic phase image set;

co-register the at least one additional phase image set to the nephrographic phase image set using a normalized mutual-information cost function to produce co-registered phase image sets;

extract, from voxel data within the region of interest in the co-registered phase image sets, a radiomics feature vector that includes shape features computed on an entire tumor volume and texture features derived from at least one of: gray-level histogram analysis, gray-level co-occurrence matrix analysis, gray-level difference/dependence matrix analysis, or frequency analysis based on a fast Fourier transform;

apply to the radiomics feature vector a trained machine-learning classifier comprising a random forest classifier that (i) ranks variables of importance using an out-of-bag Gini index and (ii) was validated using tenfold cross-validation; and output, by the processor, a probability that the renal mass is malignant and a classification of the renal mass as benign or malignant based on the probability;

wherein the trained machine-learning classifier is trained using a reduced radiomics panel that comprises radiomics features predetermined to be robust across multiple CT scanners and imaging protocols based on an intraclass correlation coefficient criterion.

14. The system of claim 13, wherein the patient clinical factors include at least one of age, gender, race, co-morbid conditions, local symptoms at diagnosis, smoking status, family history, renal function, renal mass size or tumor-specific variables.

15. The system of claim 13, wherein the texture analysis of computer-tomographic imaging includes performing two-dimensional shape and texture analysis on a largest tumor diameter within each imaging plane or performing three-dimensional shape and texture analysis on an entire tumor volume.

* * * * *